(12) United States Patent
Harvey et al.

(10) Patent No.: US 9,942,091 B2
(45) Date of Patent: Apr. 10, 2018

(54) PUMP CONFIGURATION SOFTWARE WIZARD FOR CONFIGURING PARAMETERS OF A HANDHELD INSULIN PUMP

(71) Applicant: Roche Diagnostics Operations, Inc., Indianapolis, IN (US)

(72) Inventors: Graeme Harvey, Avon, IN (US); Hans Jensen, Fishers, IN (US); James Long, Fishers, IN (US); Kaitlin Stinson, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 391 days.

(21) Appl. No.: 14/634,039

(22) Filed: Feb. 27, 2015

(65) Prior Publication Data

US 2016/0254952 A1    Sep. 1, 2016

(51) Int. Cl.
| | | |
|---|---|---|
| G06F 3/0484 | (2013.01) | |
| H04L 12/24 | (2006.01) | |
| A61M 5/142 | (2006.01) | |
| G06F 3/0482 | (2013.01) | |

(52) U.S. Cl.
CPC ..... H04L 41/0813 (2013.01); A61M 5/14244 (2013.01); G06F 3/0482 (2013.01); H04L 41/0846 (2013.01); H04L 41/0873 (2013.01); A61M 2005/14292 (2013.01); A61M 2205/50 (2013.01); A61M 2205/52 (2013.01)

(58) Field of Classification Search
CPC . H04L 41/0813; H04L 41/22; G06F 3/04842; G06F 3/04847; A61M 5/14244; A61M 2005/14292; A61M 2205/50; A61M 2205/52
See application file for complete search history.

(56) References Cited

U.S. PATENT DOCUMENTS

| | | |
|---|---|---|
| 8,118,782 B2 | 2/2012 | Remde |
| 8,771,251 B2 | 7/2014 | Ruchti et al. |
| 2010/0064257 A1* | 3/2010 | Buck ................... G06F 19/3468 715/838 |
| 2012/0185449 A1* | 7/2012 | Gould ............... G06F 17/30371 707/695 |

(Continued)

Primary Examiner — Anil Bhargava
(74) Attorney, Agent, or Firm — Harness Dickey

(57) ABSTRACT

A system for configuring an insulin pump comprising: a computing device configured to receive a source device and a destination device; the source device being configured to communicate with the computing device, wherein the source device includes a source configuration file comprising a plurality of configurable source parameters; the destination device being configured to communicate with the computing device, wherein the destination device includes a destination configuration file comprising a plurality of configurable destination parameters; and the computing device being configured to determine whether a parameter mismatch occurred based on a comparison between the source configuration file and the destination configuration file; and to copies values associated with each of the plurality of source parameters to each of the plurality of destination parameters based on i) the determination of whether a parameter mismatch occurred and ii) the comparison between the source configuration file and the destination configuration file.

20 Claims, 28 Drawing Sheets

(56) References Cited

U.S. PATENT DOCUMENTS

| | | | |
|---|---|---|---|
| 2013/0036412 A1* | 2/2013 | Birtwhistle | G06F 19/3412 717/171 |
| 2013/0238768 A1* | 9/2013 | Vaidya | H04L 67/14 709/220 |
| 2013/0254697 A1* | 9/2013 | Bush | G06F 19/3406 715/771 |

* cited by examiner

Cancel Warning Message

PUMP CONFIGURATION SOFTWARE WIZARD FOR CONFIGURING PARAMETERS OF A HANDHELD INSULIN PUMP

FIELD

The present teachings generally relate to programming insulin pumps and more specifically to pump configuration software that permits operators to transfer settings between pumps.

BACKGROUND

An insulin pump is a fluid infusion device for delivering insulin to people who suffer from diabetes. The pump, which is worn by the user and eliminates the need for multiple daily insulin injections, closely imitates a normally functioning pancreas by releasing hundreds of small doses of insulin each day into the body through an infusion set to regulate blood glucose levels. The rate of delivery of these small doses (i.e., the basal rate) varies from user to user. Indeed, even for a particular user, the basal rate varies throughout the day, and depends upon a variety of factors such as the user's internal clock, metabolism, physical health, and level of stress and exercise.

A basal rate profile consists of one or more basal rates defined to cover the 24 hours of the day (e.g., 24 hourly basal rates). Although portions of this description refer to hourly basal rates and hourly basal rate profiles, it should be understood that basal rates may cover more or less than a one hour time period. Indeed, the time periods covered by basal rates in a profile need not be equal. The concepts of the present disclosure are not limited by the duration of an individual basal rate, and the references to hourly basal rates are only exemplary. Many users use different basal rate profiles for different circumstances. For example, one basal rate profile may be used for weekdays, another profile (i.e., with different hourly basal rates) for weekends, and another profile for vacation days. These different basal rate profiles are designed to accommodate the expected differences in the user's background insulin needs resulting from variations in the user's sleep patterns, levels of exercise and stress, health condition, menstrual cycle status, etc. during such periods. Pumps also deliver (either automatically or when activated by the user) bolus doses of insulin (in addition to the basal rate) before meals or snacks to compensate for caloric intake.

As the amount and rate of insulin delivery (both basal and bolus) must be tailored to the individual needs of the user, modern pumps are programmable. Some pumps are capable of communicating with a separate computing device, and are compatible with configuration software applications that may be executed on the computing device. The configuration software permits an operator, such as the user or a health care provider, to customize the settings of the various parameters that affect the pump's operation. These parameters are included in a configuration file that is executed by the pump, and include hourly basal rates, maximum hourly basal rates, bolus dose settings, communication settings, battery settings, and many other settings and/or parameters.

For example, using configuration software, a user may upload the configuration file from the user's pump, modify the settings for certain parameters to change the operation of the pump, and save the modified configuration file to the pump. Alternatively, a health care provider responsible for programming the pumps of multiple patients may select an initial configuration file stored on a pump or computing device as a starting point for programming the patients' pumps. Many of the parameter settings of the initial configuration file (e.g., battery type, language, etc.) may be suitable for all of the pumps to be programmed. Other settings (e.g., hourly basal rates, bolus dose settings, etc.) may be unique to each patient's pump. After the health care provider selects the initial configuration file, he or she may change only the settings needed to customize the pump's operation for the current patient, then save the customized configuration file to the patient's pump without having to define a setting for every pump parameter.

As suggested by the foregoing, insulin pumps perform relatively complex functions, which directly affect the health of the user. For at least these reasons, configuration software is generally designed to simplify, to the extent possible, the processes for programming pump functions while simultaneously incorporating safety measures to prevent operators from inadvertently programming a pump with parameter settings that may harm the user. One safety measure incorporated by some configuration software applications is a workflow structure that prevents operators from selecting invalid settings for pump parameters. Many pump parameters are dependent upon one another. For example, the range of settings available for an hourly basal rate depends upon the setting of the maximum hourly basal rate parameter. Thus, conventional configuration software may prevent the operator from selecting an hourly basal rate that exceeds the current maximum hourly basal rate parameter.

Given the complexity of setting pump parameters and the importance of parameter dependence, once a user or health care provider, such as a the patient's physician, customizes the parameters in the initial configuration file, it is desirable to avoid having to reconfigure the customized configuration file. For example, a patient may replace a previously configured pump. The patient may replace the previously configured pump for any number of reasons including, but not limited to, a failure in the previous pump, in order to upgrade to a new model pump, or to downgrade to a more simplified pump. Accordingly, a system and method capable of transferring (copying) a customized configuration file from an existing pump to a replacement pump is desirable.

SUMMARY

The present approach to programming pump configuration files provides flexibility by permitting the operator to set a plurality of parameters on a replacement pump by transferring and/or copying a set of patient customized parameters from an existing pump.

A system for configuring an insulin pump includes a computing device, a source device, and a destination device. The computing device includes a processor and associated memory, the processor being configured to execute software stored on the memory. The computing device receives a selection identifying a source device and a selection identifying a destination device. The source device is configured to communicate with the computing device. The source device includes a source configuration file comprising a plurality of configurable source parameters.

The destination device is also configured to communicate with the computing device. The destination device includes a destination configuration file comprising a plurality of configurable destination parameters. The computing device is configured to retrieve the source configuration file and the destination configuration file and to determine whether a parameter mismatch occurred based on a comparison between the source configuration file and the destination configuration file. The computing device copies values associated with each of the plurality of source parameters to each of the plurality of destination parameters based on i) the determination of whether a parameter mismatch occurred and ii) the comparison between the source configuration file and the destination configuration file.

BRIEF DESCRIPTION OF THE DRAWINGS

The present disclosure will become more fully understood from the detailed description and the accompanying drawings, wherein.

Corresponding reference characters indicate corresponding parts throughout the several views.

DETAILED DESCRIPTION

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

It should be understood that although the concepts below are described as relating to insulin pump configuration software, such as the ACCU-CHEK® 360° Insulin Pump Configuration Software provided by Roche Diagnostics Corporation, the concepts may also relate to diabetes management software systems for tracking and analyzing health data, such as, for example, the ACCU-CHEK® 360 Diabetes Management System provided by Roche Diagnostics Corporation. Moreover, the concepts described herein may also have applicability to apparatuses, methods, systems, and software in fields that are unrelated to healthcare. Furthermore, it should be understood that references in this patent application to devices, pumps, meters, monitors, or related items are intended to encompass any currently existing or later developed apparatus that includes some or all of the features attributed to the referred to apparatus, including but not limited to the ACCU-CHEK® Insight, ACCU-CHEK® Active, ACCU-CHEK® Aviva, ACCU-CHEK® Compact, ACCU-CHEK® Compact Plus, ACCU-CHEK® Integra, ACCU-CHEK® Go, ACCU-CHEK® Performa, ACCU-CHEK® Spirit, ACCU-CHEK® D-Tron Plus, and ACCU-CHEK® Voicemate Plus, all provided by Roche Diagnostics Corporation or divisions thereof.

Figure 1:
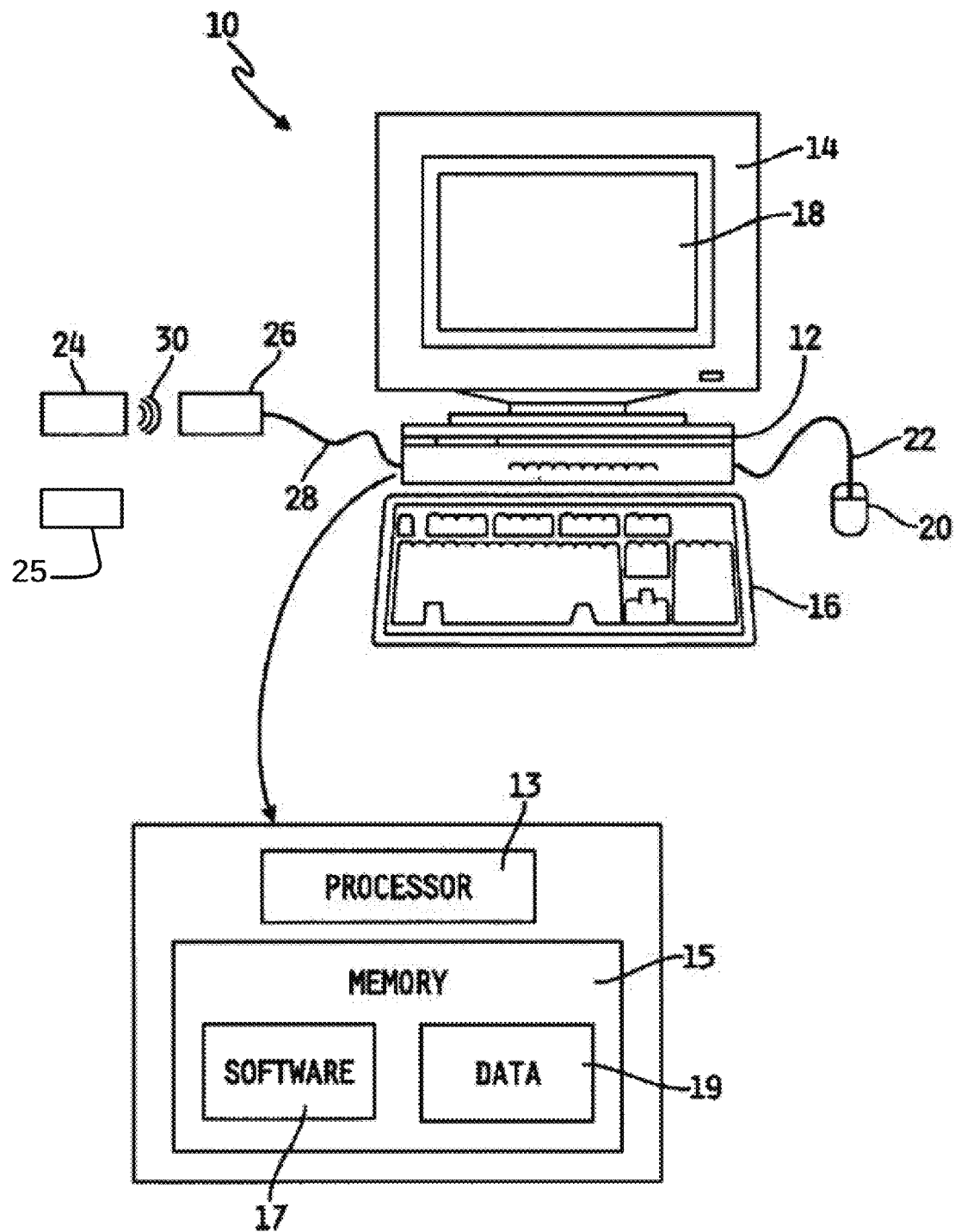
FIG. 1 is a conceptual diagram of a computing device in communication with an insulin pump.

Turning now to the figures, FIG. 1 depicts an exemplary embodiment of a system 10, some or all of the components of which may be used in conjunction with the teachings of the present disclosure. System 10 generally includes a computing device 12, shown here in the form of a computer having display device 14, in this case a computer video screen or monitor having screen 18, a keyboard 16, a processor 13, and memory 15, which may contain the configuration software 17 of the present disclosure and data 19 as is further described herein. While described and depicted herein with specific reference to a computer, certain concepts of the present disclosure may be utilized in conjunction with any computing device capable of operating pump programming software, such as a laptop computer, mobile tablet, and/or mobile phone. Computing device 12 also has a pointing device or mouse 20 connected to it by cable 22 (or wirelessly). While mouse 20 and keyboard 16 are shown, system 10 may include any input device such as a touchpad, joystick, touch screen, trackball, voice command, etc.

Computing device 12 may include a variety of computer-readable media. Computer-readable media can be any available media that can be accessed by computing device 12 and includes both volatile and non-volatile media, and removable and non-removable media. By way of non-limiting example, computer-readable media may comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules and other data and which can be accessed by computing device 12. Computer-readable media may be accessed directly or through a network such as the Internet.

System 10 is configured to provide information to, and receive information from, infusion pump 24, hereinafter referred to as a source pump 24. Again, while an infusion pump, and more particularly an insulin pump, is described herein, it should be understood that the teachings of the present disclosure may also apply to devices such as "smart" insulin pens or other such devices known or hereafter developed.

In FIG. 1, computing device 12 is shown coupled to communication media or dongle 26, in this case a modulated signal transceiver, accessible to computing device 12 by means of cable 28, and configured to transmit and receive modulated signal 30 to establish logical communication with the source pump 24. In another exemplary embodiment, computing device 12 and the source pump 24 may include ports configured to establish a physical connection. By way of non-limiting example, dongle 26 may include wired media such as a wired network or direct wired connection, and wireless media such as acoustic, RF, infrared and other wireless media. More specifically, dongle 26 as depicted includes an infrared port for communication with a similar infrared port of the source pump 24.

It is understood that while only limited examples are described, the computing device 12 may connect to multiple devices (i.e., insulin pumps or other suitable devices) in a variety of connect protocols such as infrared, BlueTooth, WiFi, USB, wired, proprietary cable connection, generic cable connection, and/or any other suitable connection type or protocol. It is also understood that the computing device 12 may be connected to multiple devices simultaneously via one or more of the above mentioned connection types and/or protocols. Further, in some examples, a controller (not shown) may be connected to the computing device 12 via a USB cable. The operator may configure a configuration file stored on the controller. The controller may then communicate, wirelessly, with the source pump 25 in order to apply the copy the configuration file to the source pump 25. In this manner, the operator indirectly configures the source pump 25 by first modifying the configuration file on the controller.

FIG. 1 also illustrates a destination pump 25. The destination pump 25 will be described in greater detail below. It is understood that the destination pump 25 includes similar features to those described above with reference to the source pump 24. In some implementations, the destination pump 25 may be a replacement pump for the source pump 24. For example only, a user of the source pump 24 may replace the source pump 24 due to a failure in the source pump 24, a desire to upgrade to different module pump, or any other suitable reason for replacing the source pump 24 with the destination pump 25.

Figure 2:
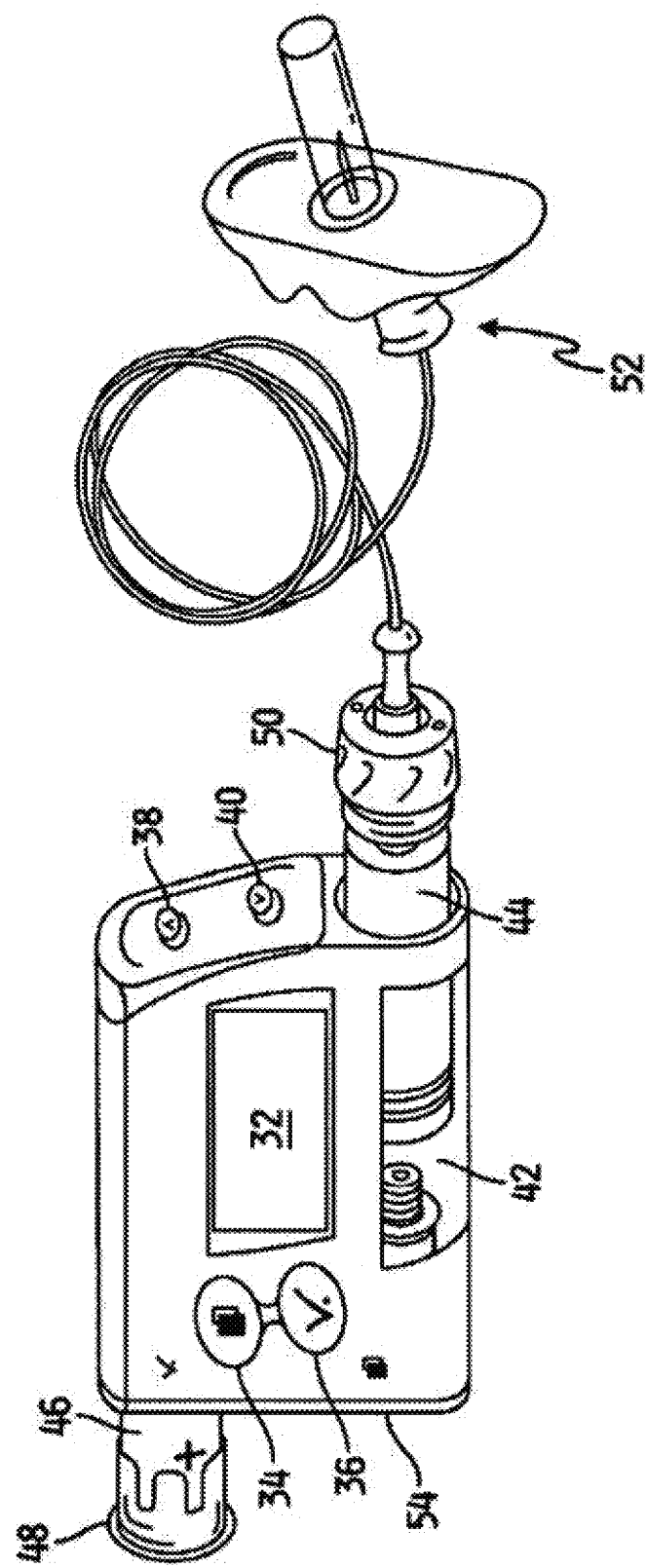
FIG. 2 is perspective view of an insulin pump coupled to an infusion set.

Referring now to FIG. 2, each of the source pump 24 and the destination pump 25 includes a display 32 for displaying information to an operator or user, a menu button 34 for navigating though the various functions provided by the source pump 24 and/or the destination pump 25, a check button 36 for selecting options, an up key 38 and down key 40 for scrolling through options and controlling certain insulin delivery functions, a cartridge receptacle 42 for storing an insulin cartridge 44, a battery 46 (shown partially inserted), a battery cap 48 (shown unsecured pump), an adapter 50 for physically coupling cartridge 44 to an infusion set 52, and a communication port, such as an internal radio interface (not shown) for sending information to, or receiving information from, computing device 12 through dongle 26.

Figure 3:
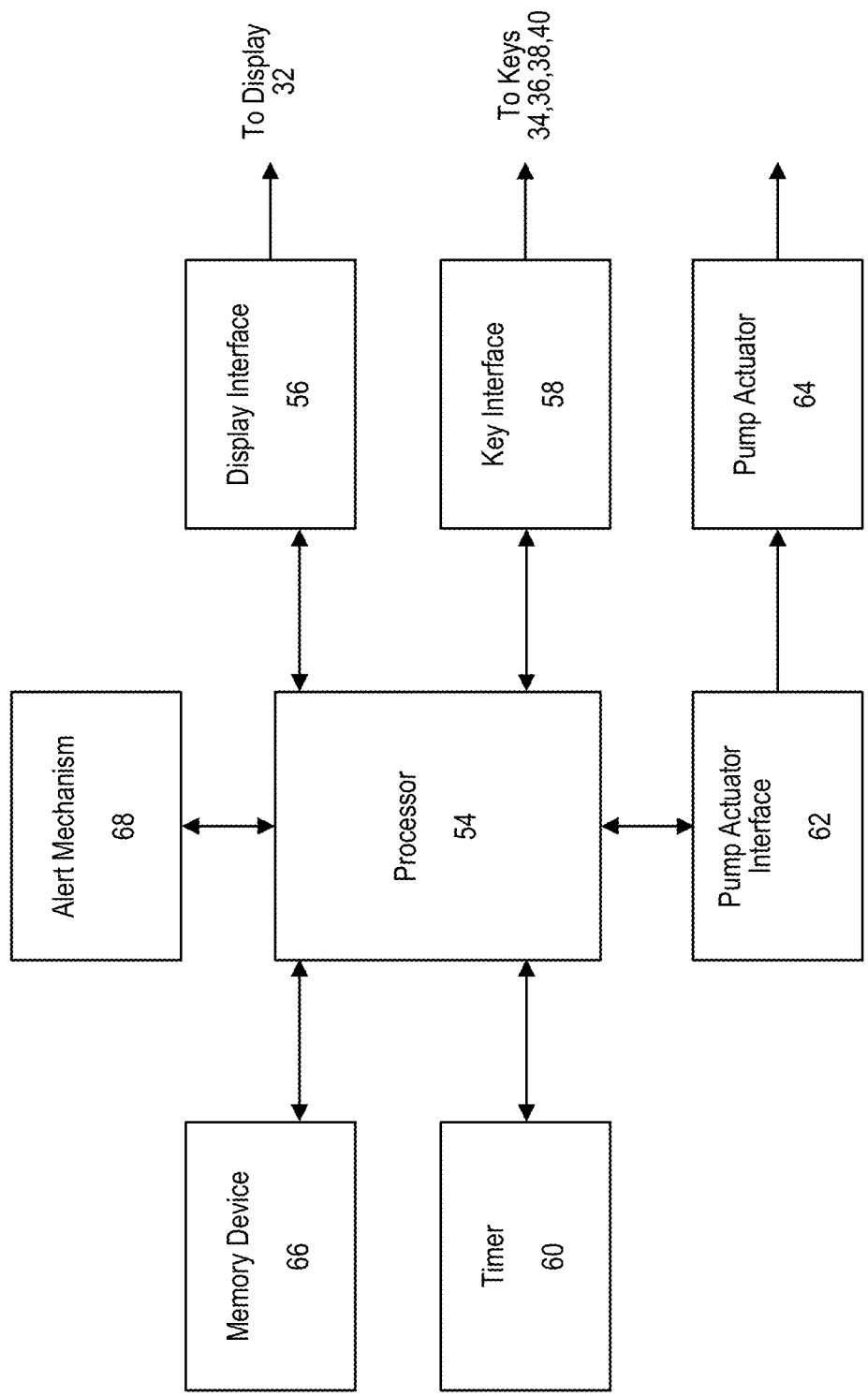
FIG. 3 is a block diagram of internal components of the pump of FIG. 2.

FIG. 3 provides a block diagram representation of internal components of the source pump 24 and the destination pump 25. As shown, each of the source pump 24 and the destination pump 25 includes a processor 54 coupled to a display interface 56, which is coupled to display 32. Processor 54 is also coupled to a keypad interface 58 which is coupled to keys 34, 36, 38, 40, and a pump actuator interface 62 which is coupled to an actuator 64 suitable for delivering insulin doses (medical infusion pumps other than insulin pumps will deliver doses of other medicament). Processor 54 is further coupled to a memory device 66 that stores application programs and data, including the configuration files described herein. Memory device 66 is constructed of any combination of volatile and/or nonvolatile memory suitable for a particular embodiment. Processor 54 is also coupled to an alert mechanism 68, that, in various embodiments is a buzzer, a vibrator, a light emitting diode, or the like, suitable for providing audible, tactile, or visual alerts to an insulin pump user. Finally, processor 54 is coupled to a timer 60, which is capable of maintaining a current time, including time of day and day of the week.

For the purpose of the illustrative example of the operation of configuration software 17, assume the operator is a health care provider who desires to customize a configuration file stored on the source pump 24. In this example scenario, the operator will read a configuration file from the source pump 24 and adjust at least one of a plurality of parameters within the configuration file. For example, the operator may change preset maximum hourly basal rate to a customized maximum hourly basal rate determined specifically for the user of the source pump 24. While only a maximum hourly basal rate parameter is described, the operator may modify any of the plurality of parameters. The operator then saves and/or uploads the configuration file, via configuration software 17, to the source pump 24.

At some time subsequent to the operator programming the source pump 24, the user of the source pump 24 may desire to change, replace, or upgrade the source pump 24. For example, the user of the source pump 24 may upgrade to a new model pump, replace the source pump 24 with a similar pump due to a failure in the source pump 24, or any suitable reason for replacing the source pump 24. In one implementation, the user replaces the source pump 24 with the destination pump 25. As described above, the source pump 24 and the destination pump 25 may include similar features such as those described with reference to FIG. 3. In some instances, the destination pump 25 may include a higher resolution screen, a faster processor, or additional features to those of the source pump 24.

Having previously customized the plurality of parameters in the configuration file stored on the source pump 24, the user of the source pump 24 may desire to transfer and/or copy the parameter settings to the destination pump 25. In the example scenario, the configuration software 17 includes a copy settings module. An operator, such as a heath care provider or the user of the pump, accesses a plurality of display screens generated by the copy settings module in order to transfer the plurality of parameter settings from the source pump 24 to the destination pump 25. It is understood that while only transferring and/or copying parameter settings from the source pump 24, the configuration software 17 is capable of carrying out a variety of procedures including, but not limited to, configuring a Bolus Advisor.

Figure 4:
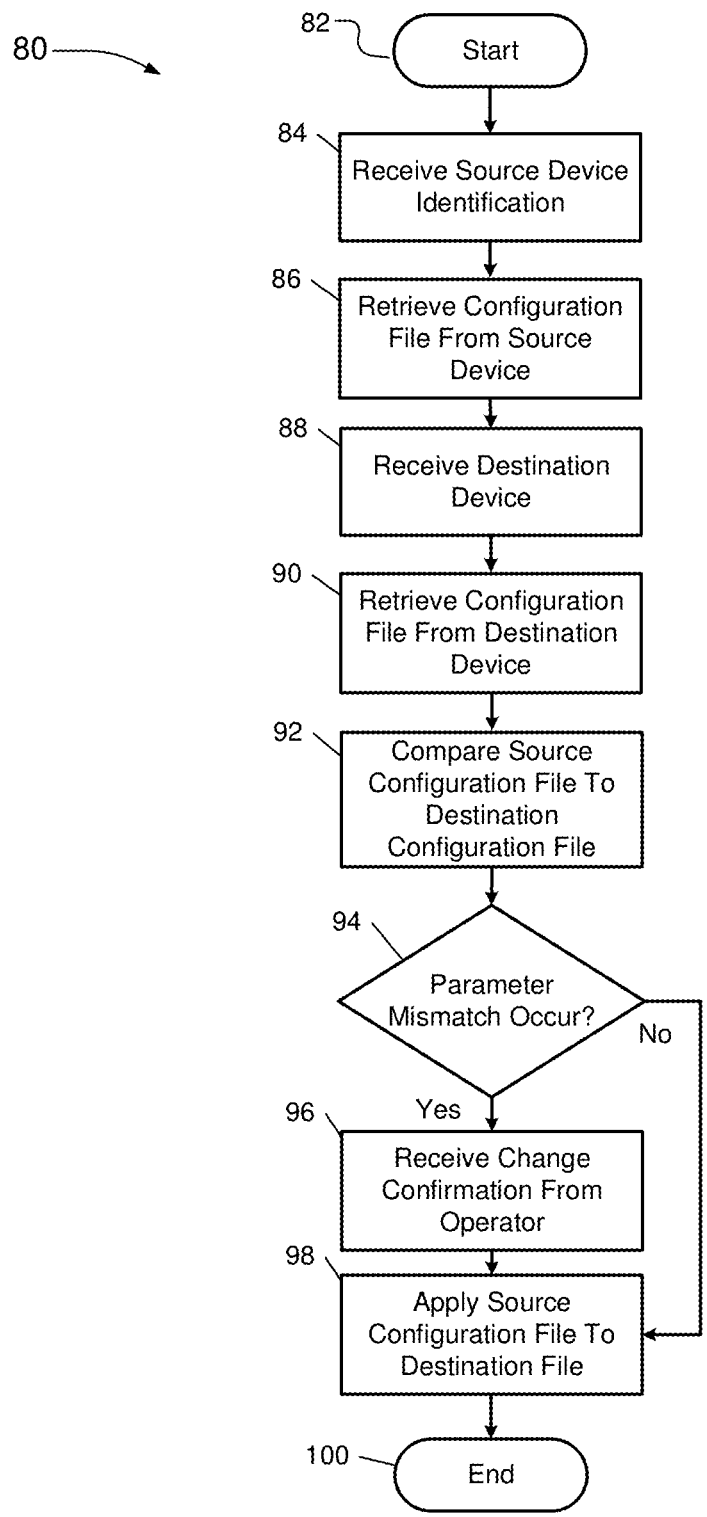
FIG. 4 is a flow diagram illustrating an example technique for copying parameters from a source device to a destination device using a copy settings module according to the principles of the present disclosure.

With reference to FIG. 4 a flow diagram illustrating an example method 80 for copying parameters from a source device to a destination device using a copy settings module begins at 82. At 84, the copy settings module receives a source device identification. For example, the copy settings module receives a device signal indicating a source device, such as the source pump 24. At 86, the copy settings module retrieves a configuration file from the source pump 24. For example, the copy settings module copies the configuration file from the source pump 24 and stores the configuration file in an associated memory. The configuration file includes a plurality of source parameters that were previously customized by an operator of the source pump 24 to a meet the medical needs of a user of the source pump 24.

At 88, the copy settings module receives a destination device identification. For example, the copy settings module receives a device signal indicating a selected destination device, such as the destination pump 25. At 90, the copy settings module retrieves a configuration file associated with the destination pump 25. The configuration file includes a plurality of destination parameters each set to an initial value. In other words, the values associated with the plurality of destination parameters are set to an initial or generic value and not customized to the user of the destination pump 25

At 92, the copy settings module compares the source configuration file to the destination configuration file. For example, the copy settings module compares each of the plurality of source parameters with each of the plurality of destination parameters. At 94, the copy settings module determines if a parameter mismatch occurred. For example, the copy settings module determines whether one or more of the source parameters does not have a one-to-one match in the destination parameters.

By way of non-limiting example, a parameter mismatch may occur when a source pump has a Temporary Basal Rate Maximum Adjustment parameter range adjustable between 0%-500% and a destination pump has a Temporary Basal Rate Maximum Adjustment parameter range adjustable between 0%-250%. In this example, the copy settings module may notify the operator that a range mismatch occurred for one for parameters. The operator will be prompted to accept a change to accommodate the variance in range or alternatively, the operator may enter a range that falls within the destination parameter range. In another example, the Temporary Basal Rate Maximum Adjustment source parameter may be set to a value that is outside the Temporary Basal Rate Maximum Adjustment destination parameter. By way of non-limiting example, the source parameter may be set to 300%, while the destination range is limited to a maximum of 250%. As described above, the operator will be prompted to accept a change to accommodate the lower upper limit of the destination parameter or alternatively, the operator may enter a value that falls within the destination parameter range.

In other words, the source pump 24 is capable of accepting a wider range for the Temporary Basal Rate Maximum Adjustment parameter than that of the destination pump 25. Other examples include, but are not limited to, a source pump having a Maximum Dose parameter set to 0 U-50 U and the destination pump having a Maximum Amount parameter capable of having a value of 1 U-25 U. It is understood the previous examples are for illustrative purposes only, and in no way limit the scope of possible parameter mismatches detected while copying a configuration file from a source pump to a destination pump.

If false, the copy settings module continues to 98. If true, the copy settings module continues at 96. At 96, the copy settings module receives a change confirmation from the operator. For example, the copy settings module informs the operator of the parameter mismatch. The copy settings module requests that the operator review the parameter mismatch and confirm a suggested modification to the value of the destination parameter corresponding to the mismatched source parameter. Alternatively, the operator may enter a value in order to correct the parameter mismatch. The copy settings module receives a confirmation from the operator. At 98, the copy settings module copies values from the source parameters to the corresponding destination parameters, including any modified parameter mismatches. The method 80 ends at 100.

Figure 5A:
FIGS. 5A-5C are screenshots illustrating a startup selection screen and a copying device settings instruction screen according to teachings of the present disclosure.
Figure 5B:
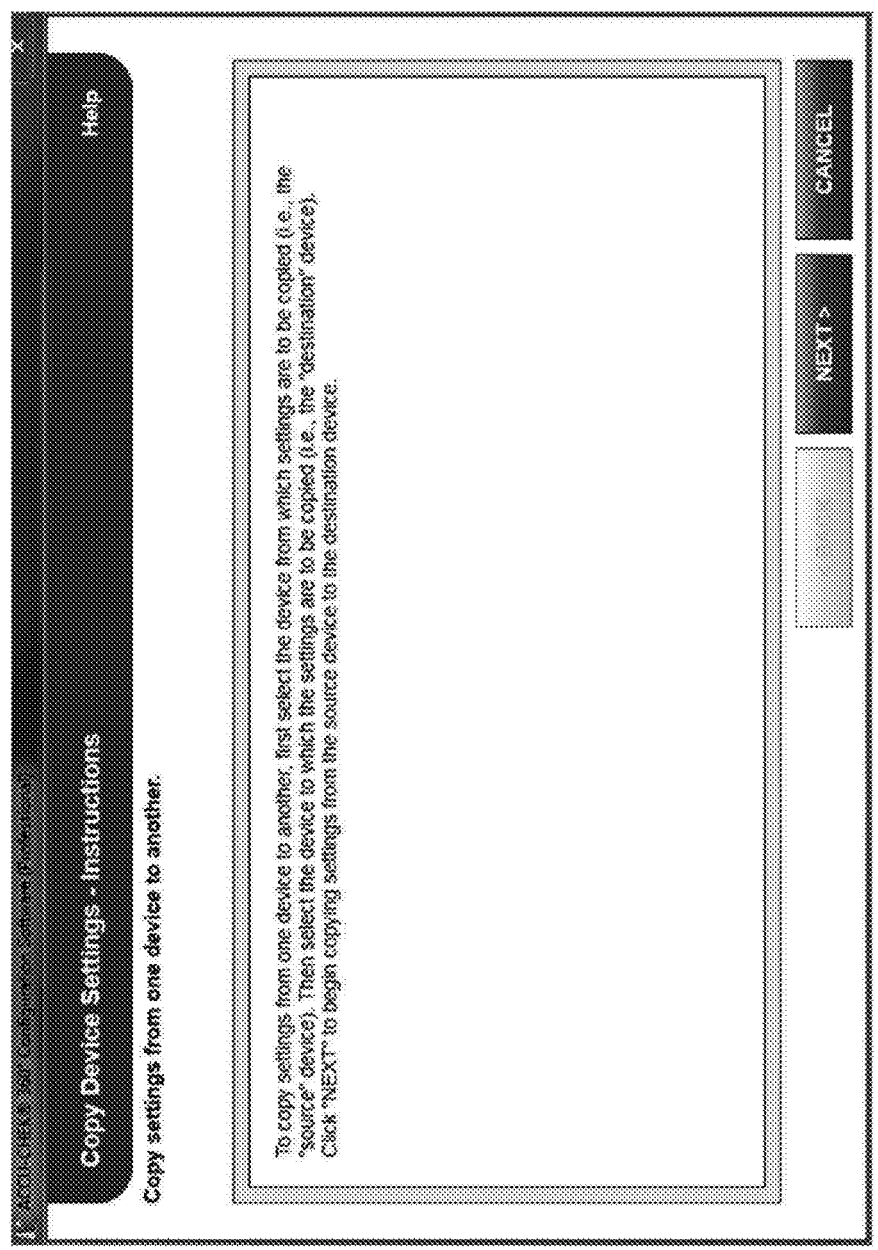
Figure 5C:
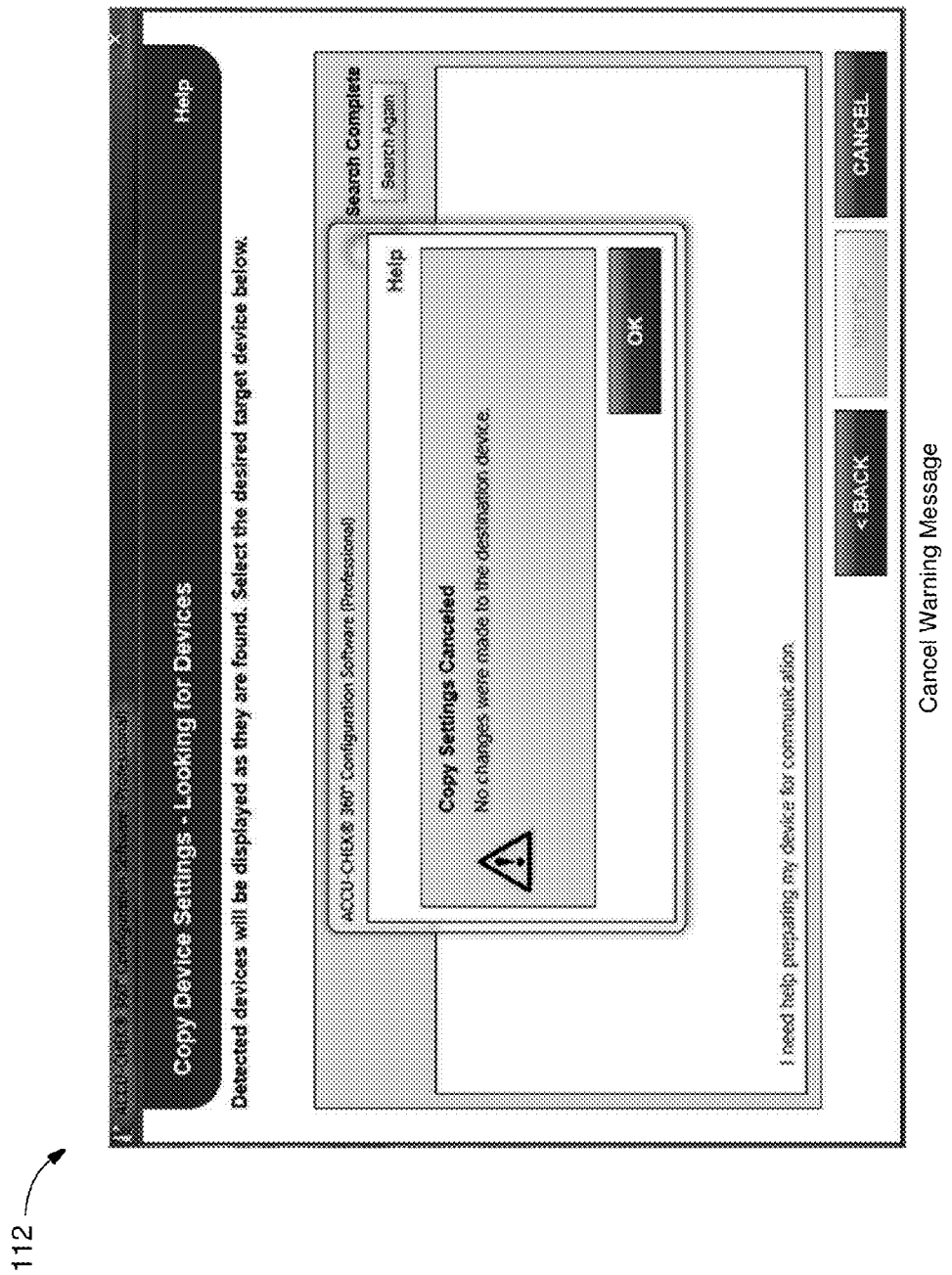
Figure 6A:
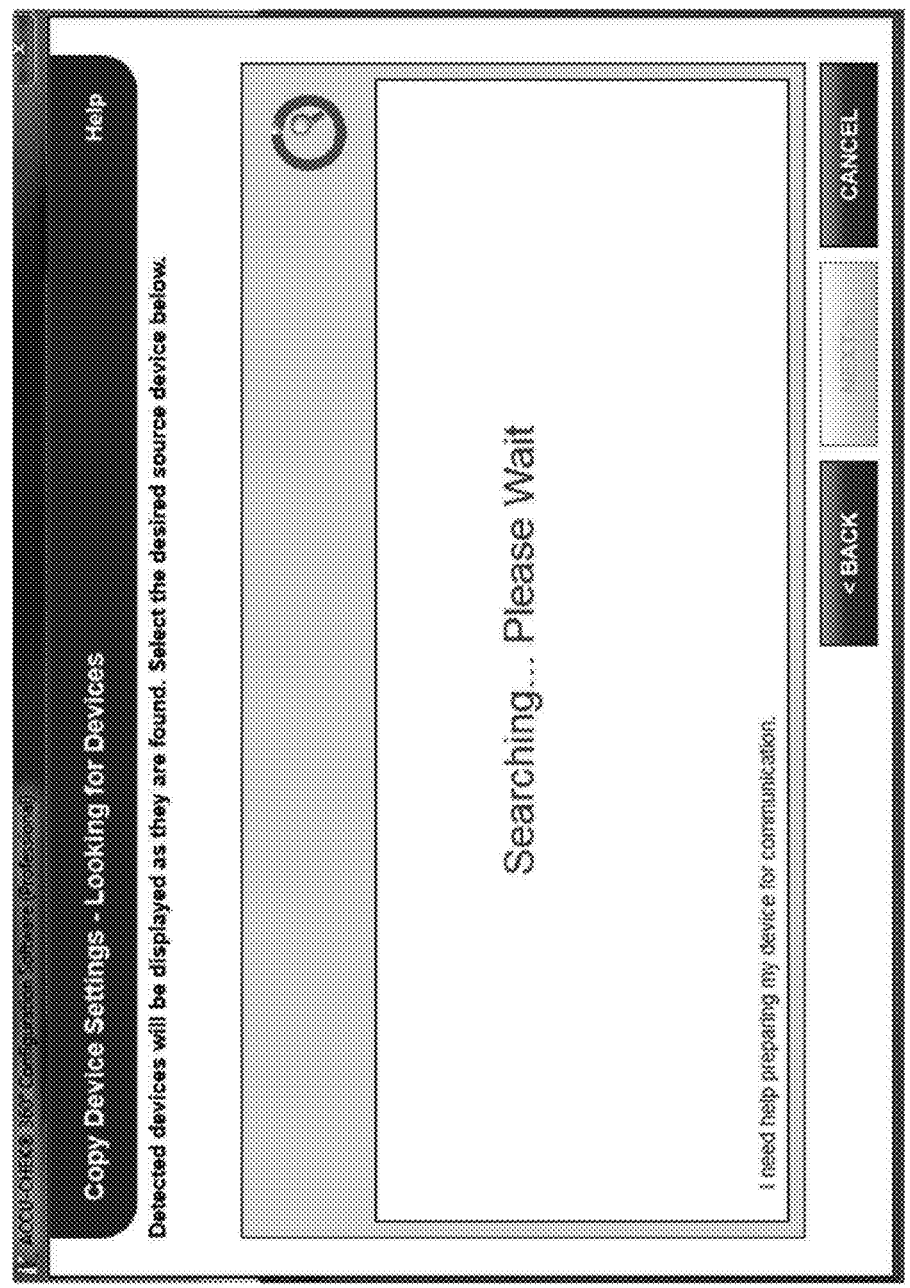
FIGS. 6A-6G are illustrations of screenshots that a user would interact with in order to select a source device for copying parameters from the source device according to teachings of the present disclosure.
Figure 6B:
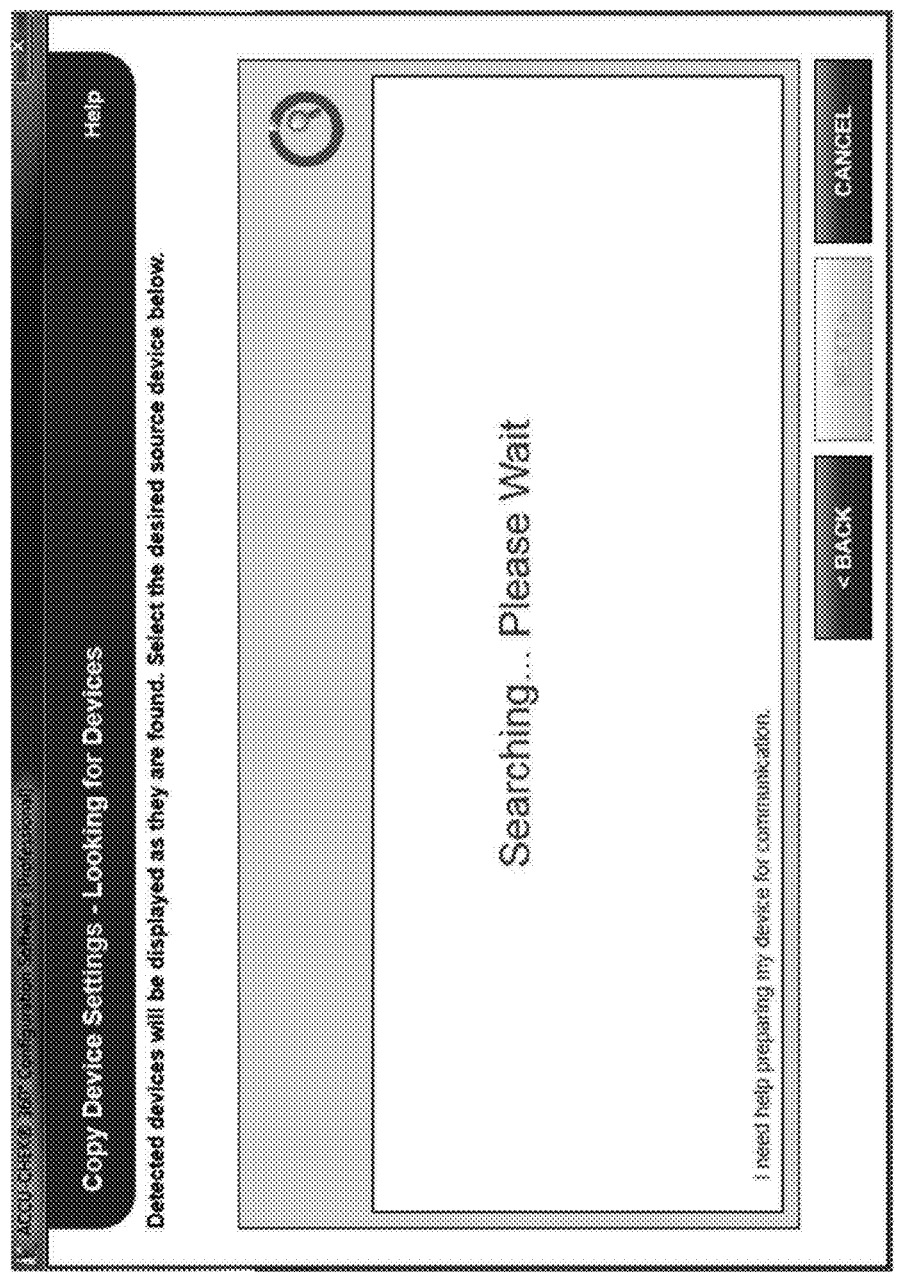
Figure 6C:
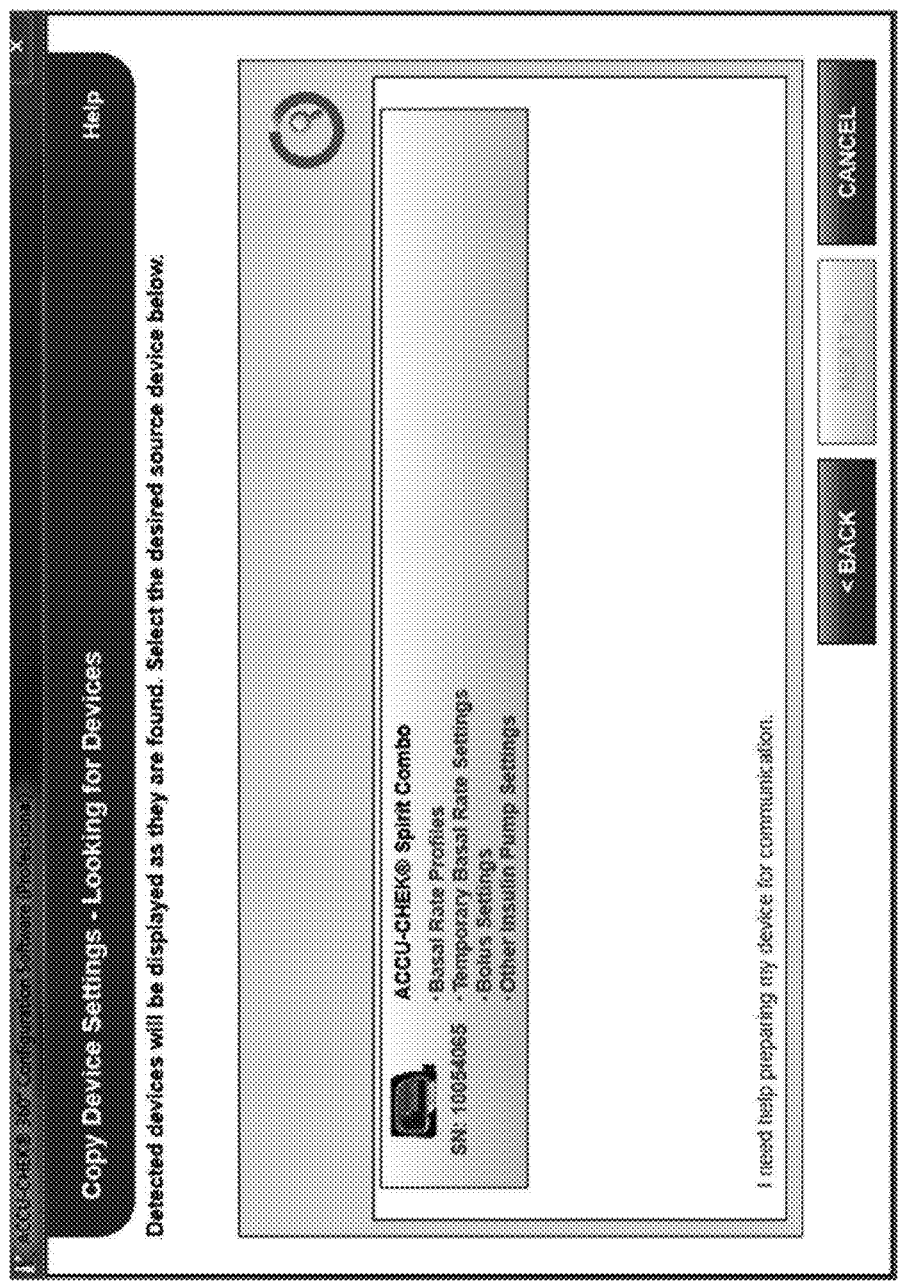
Figure 6D:
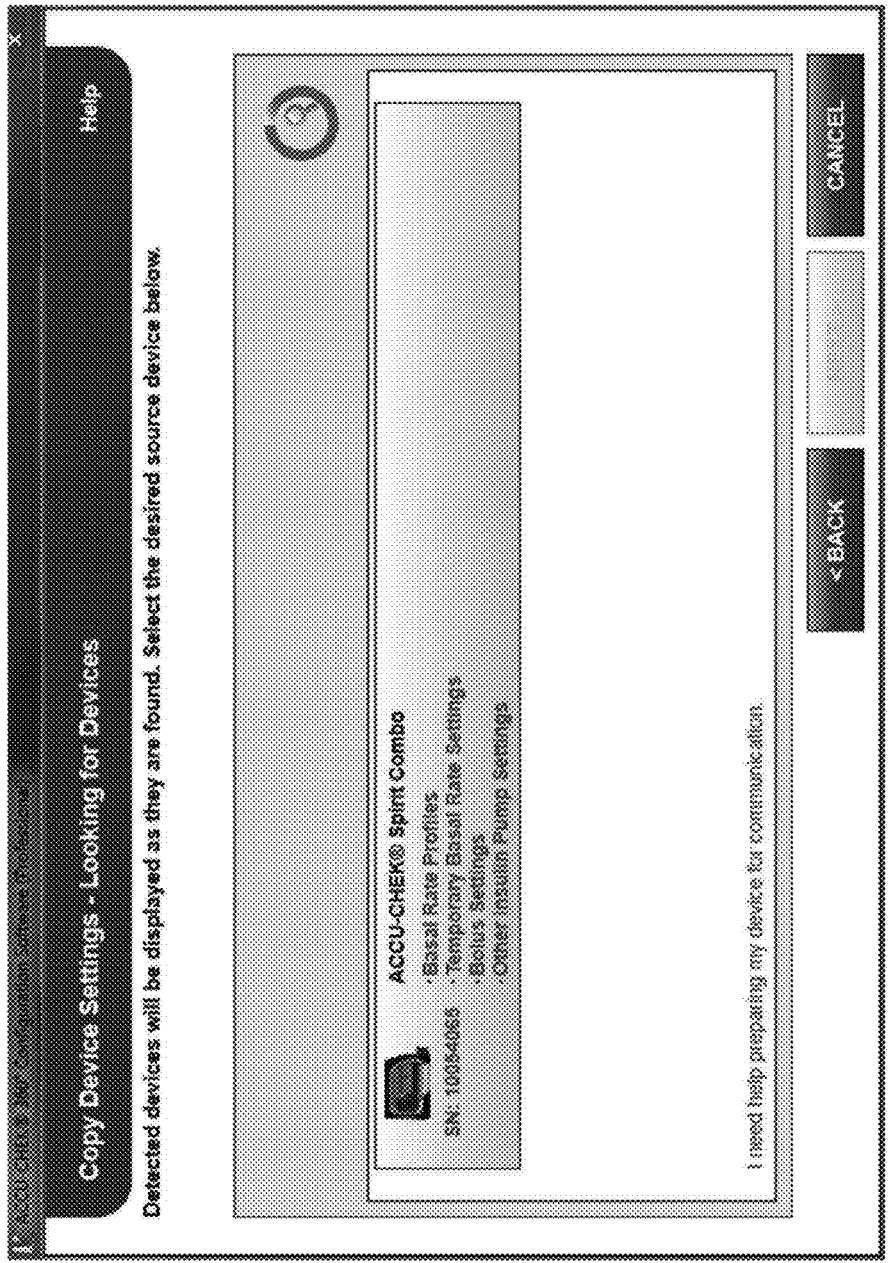
Figure 6E:
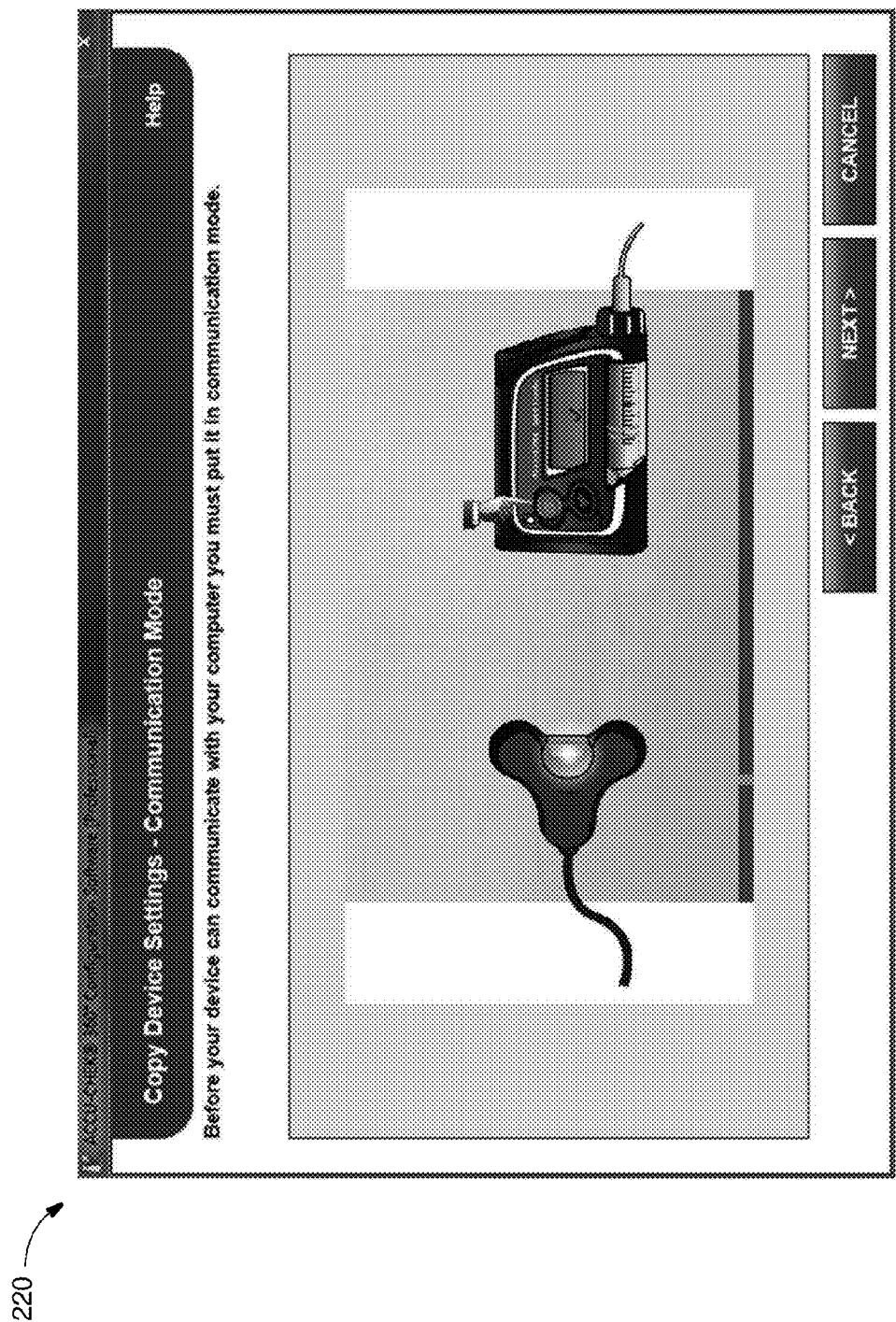
Figure 6F:
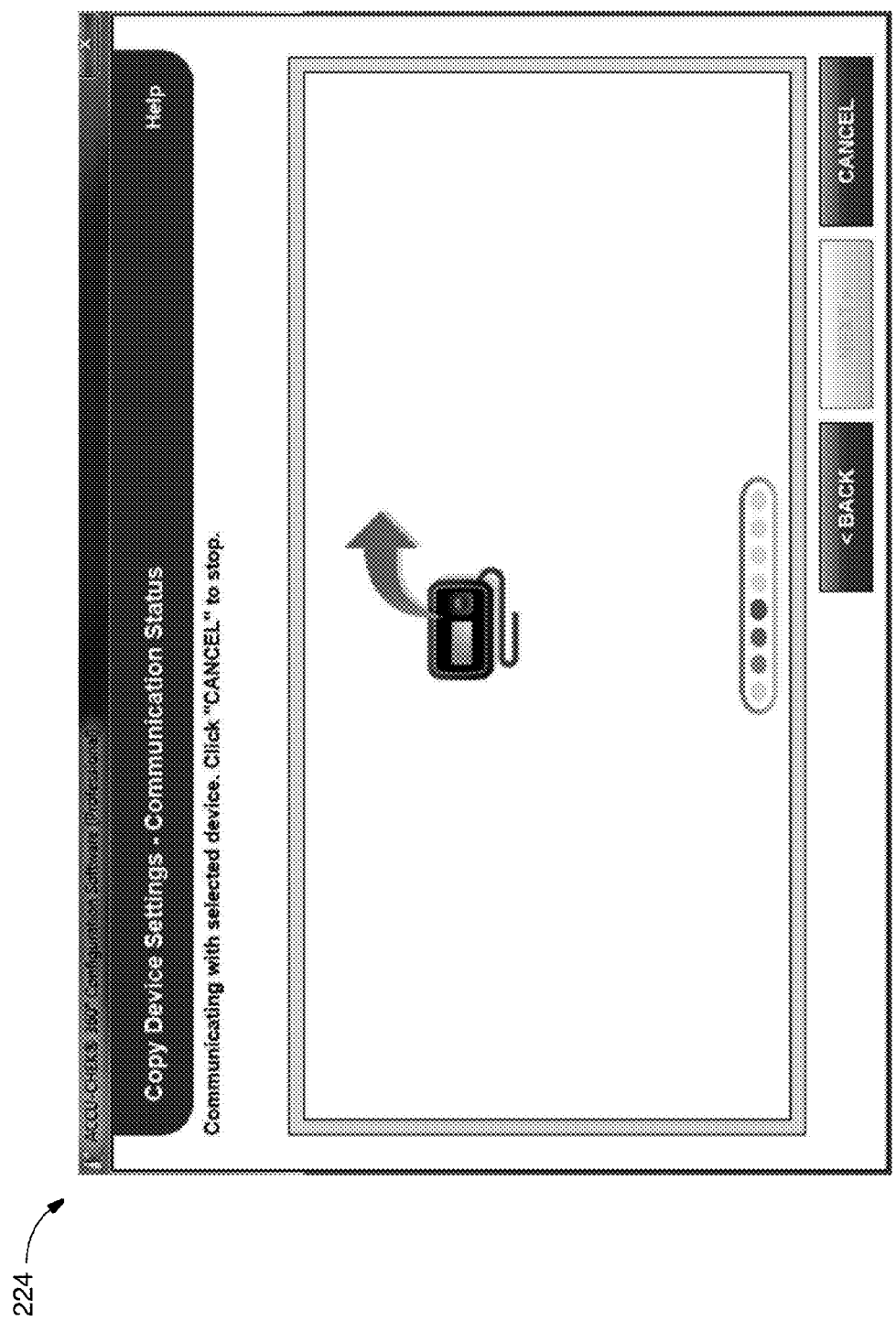
Figure 6G:
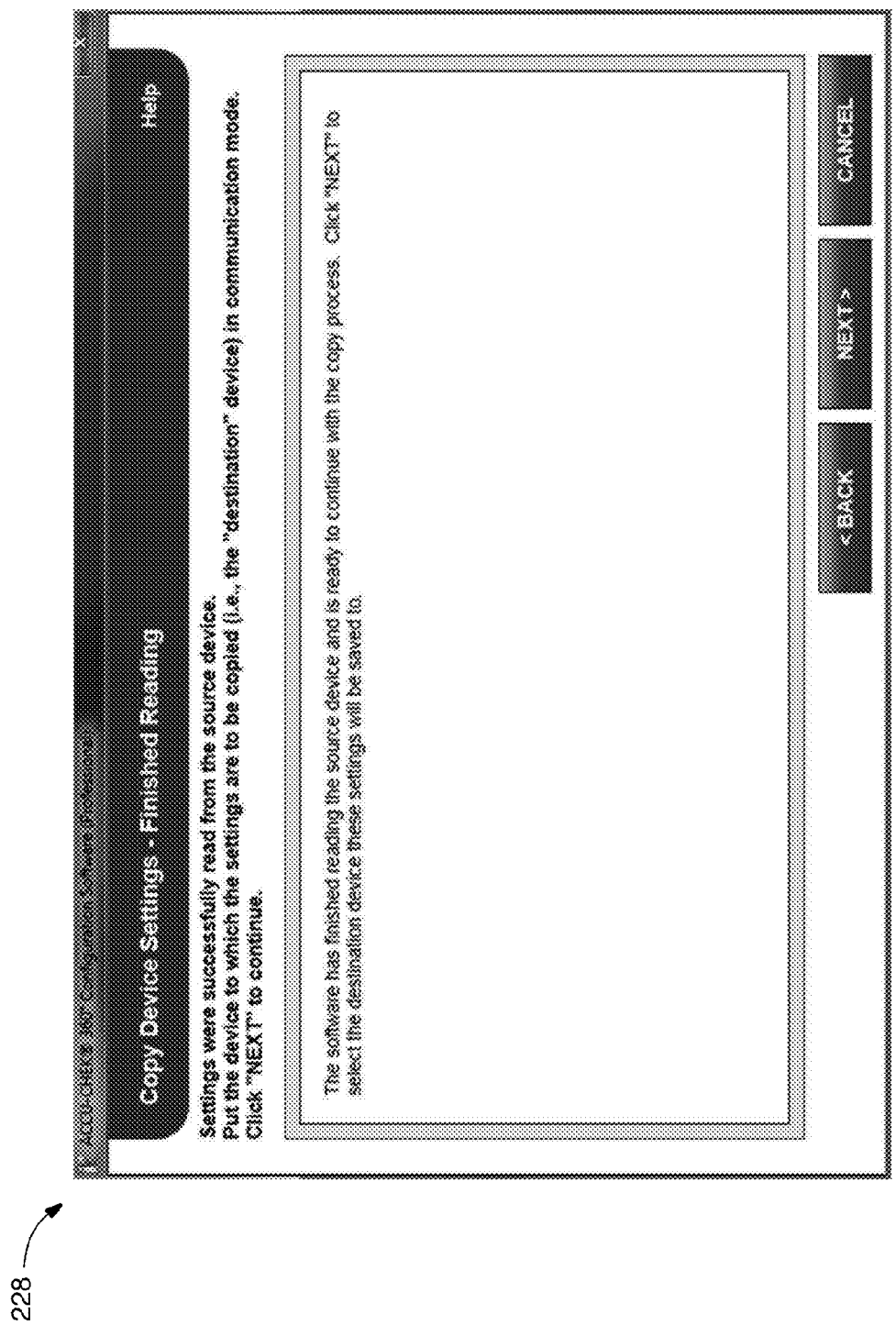
Figure 7A:
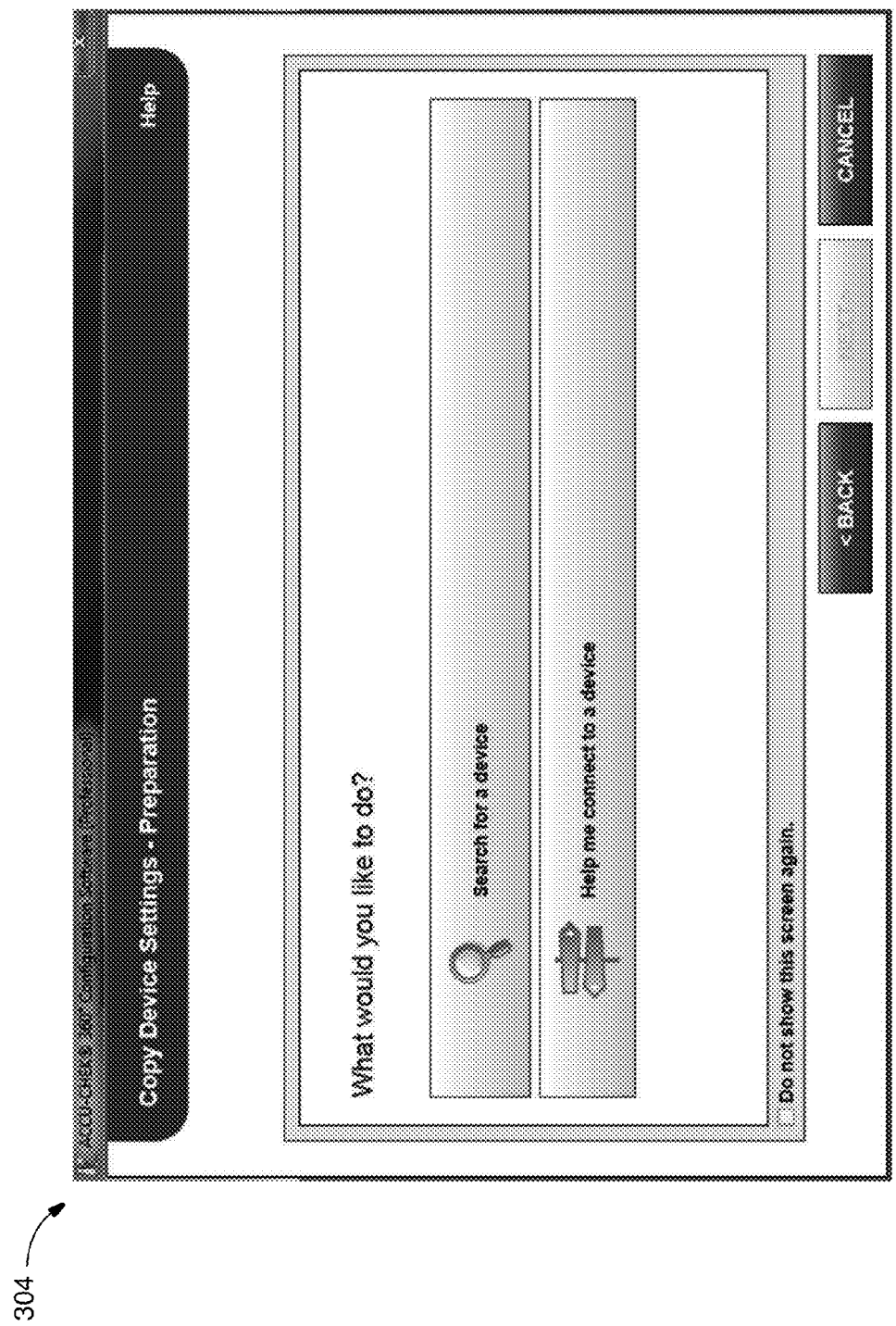
FIGS. 7A-7F are illustrations of screenshots that a user would interact with in order to select a destination device for applying the copied parameters from the source device according to teachings of the present disclosure.
Figure 7B:
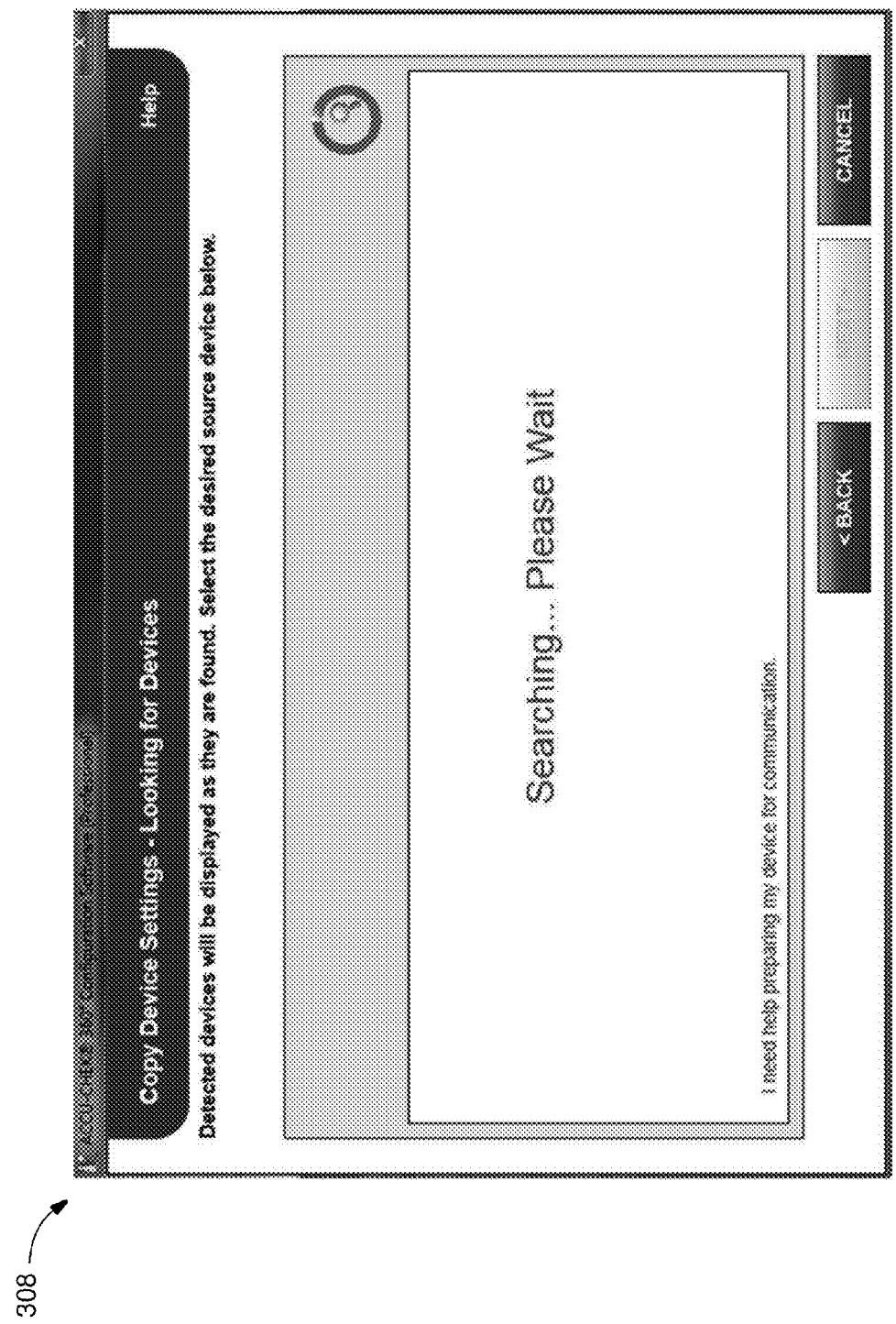
Figure 7C:
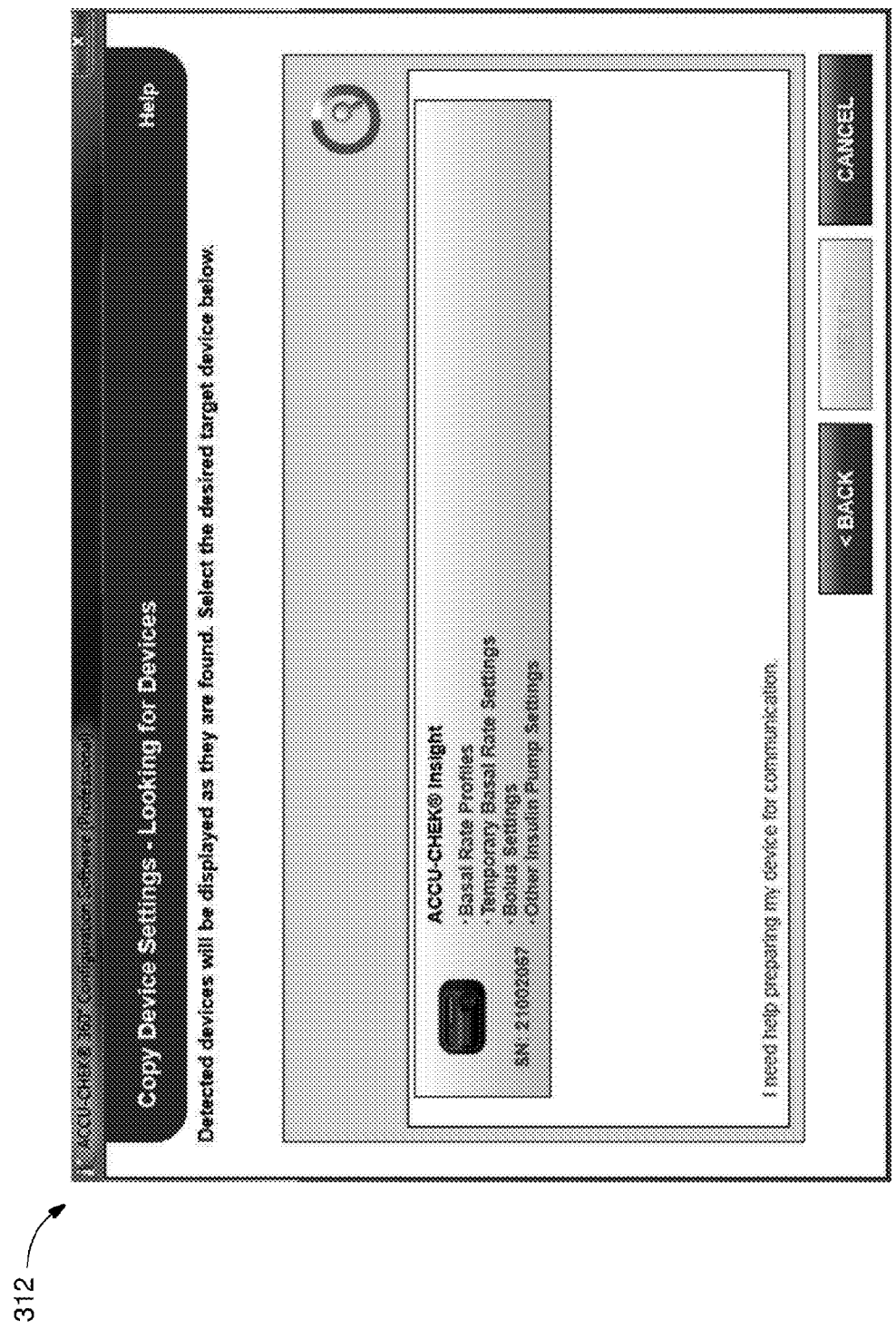
Figure 7D:
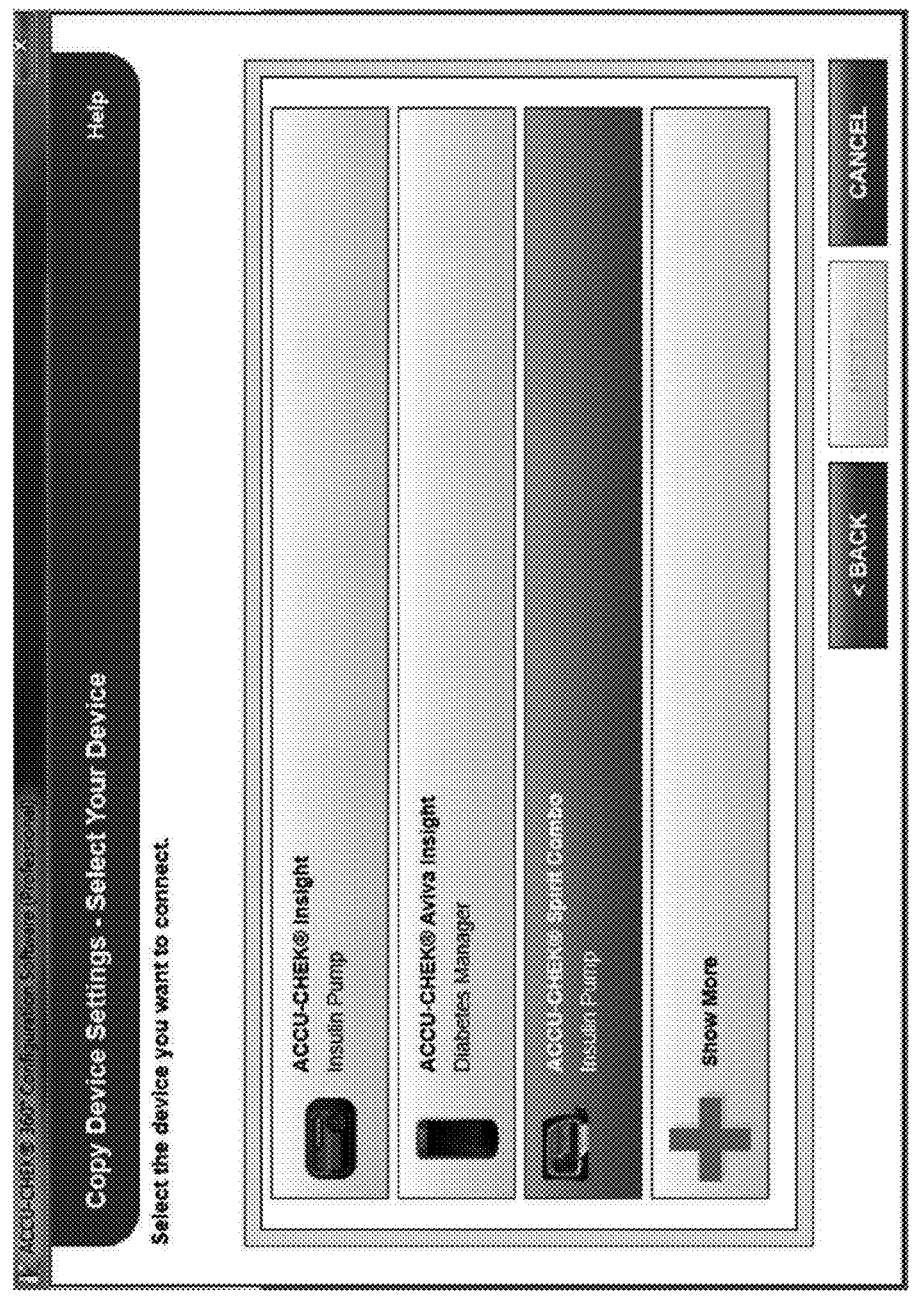
Figure 7E:
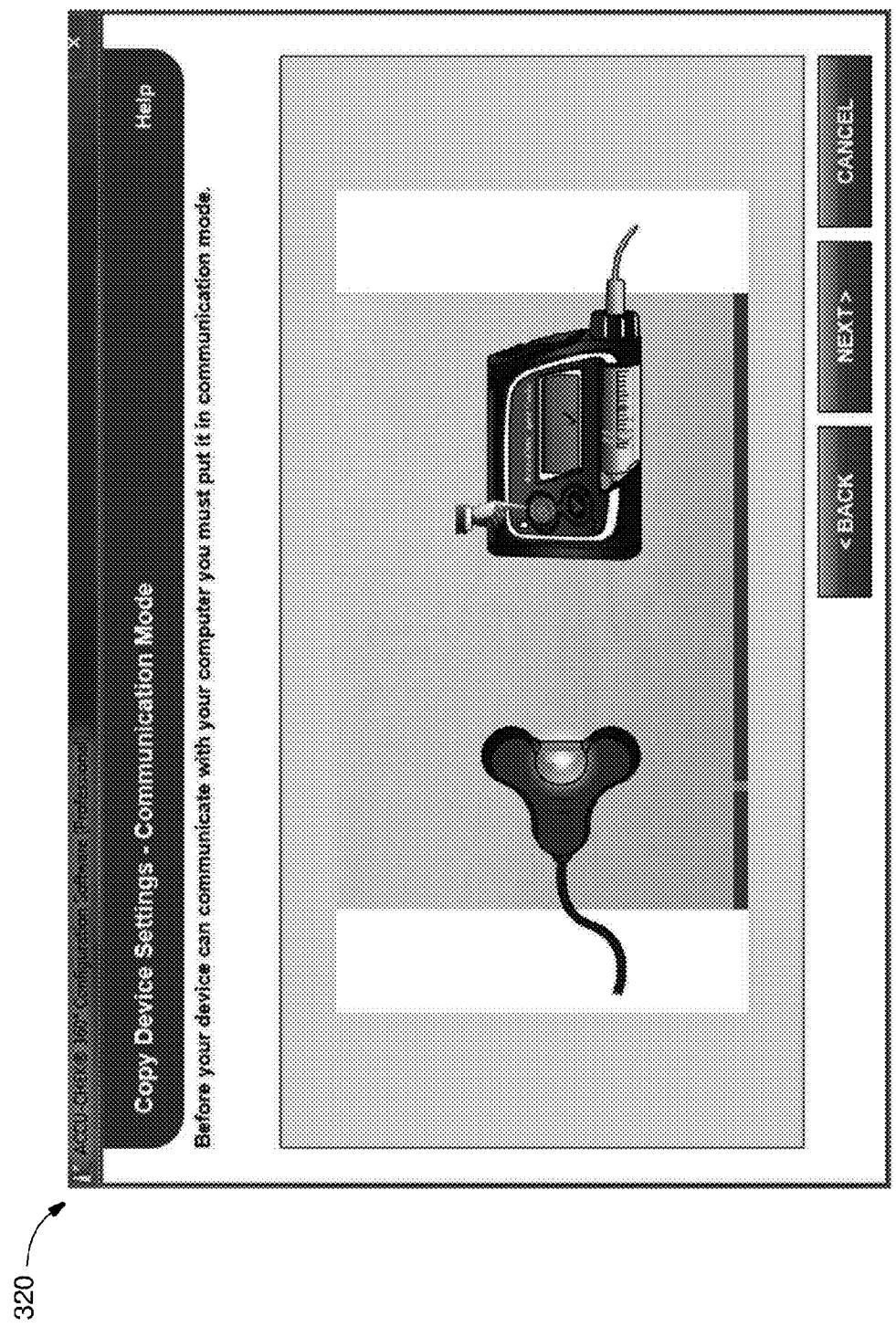
Figure 7F:
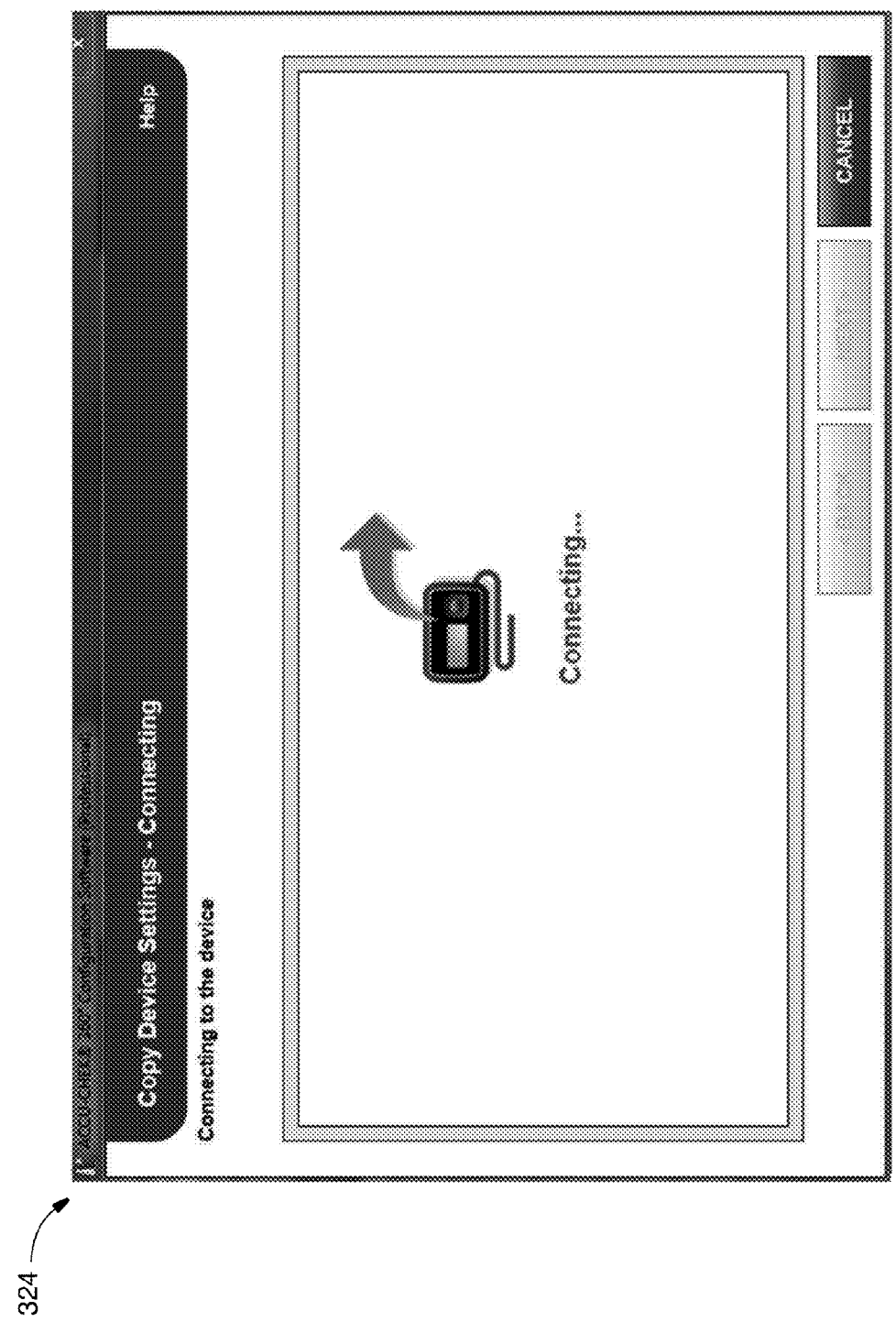
Figure 8A:
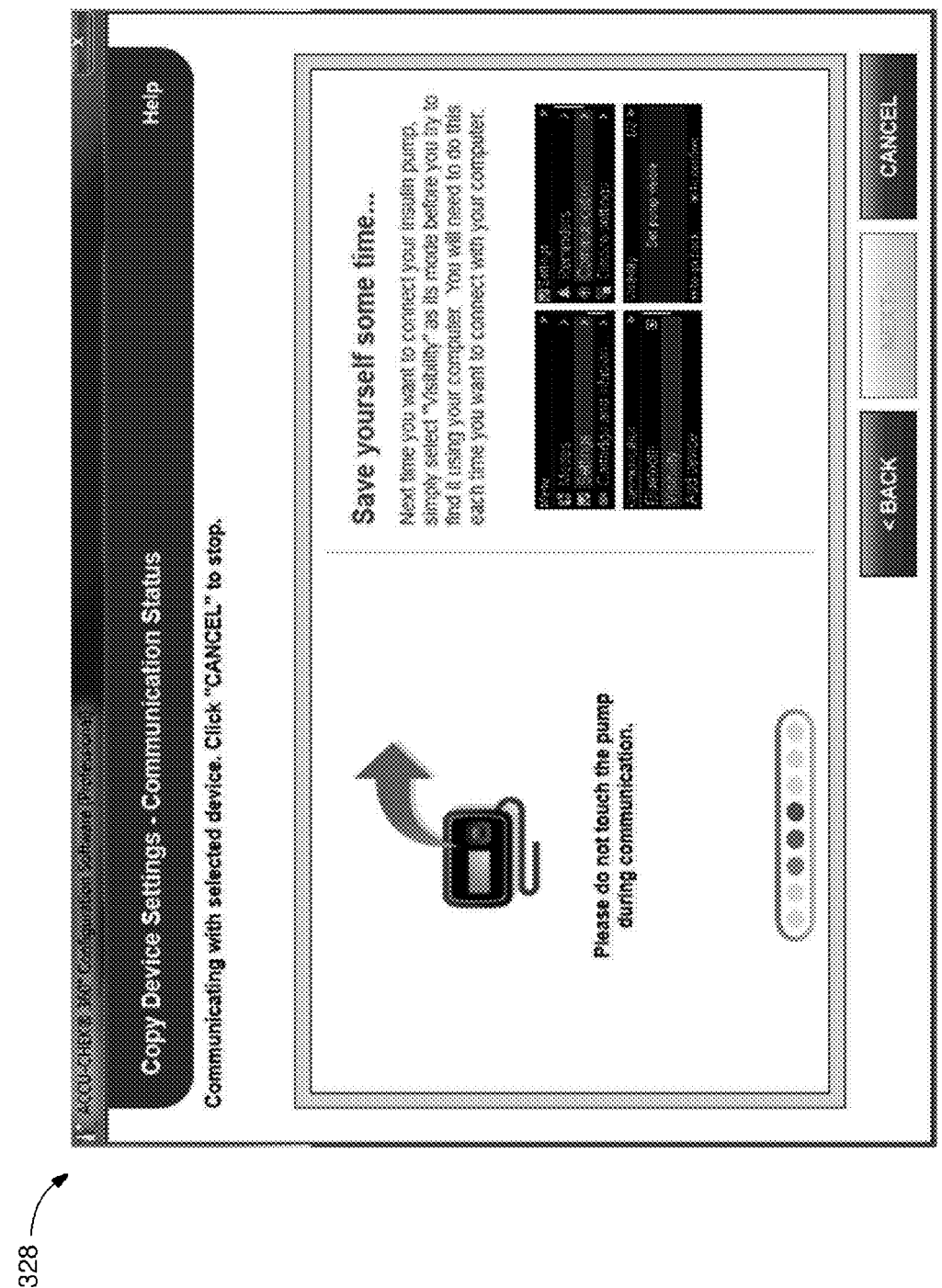
FIGS. 8A-8F are illustrations of screenshots that a user would interact with in order to resolve conflicts between the parameters copied from the source device and the parameters on the destination device according to teachings of the present disclosure.
Figure 8B:
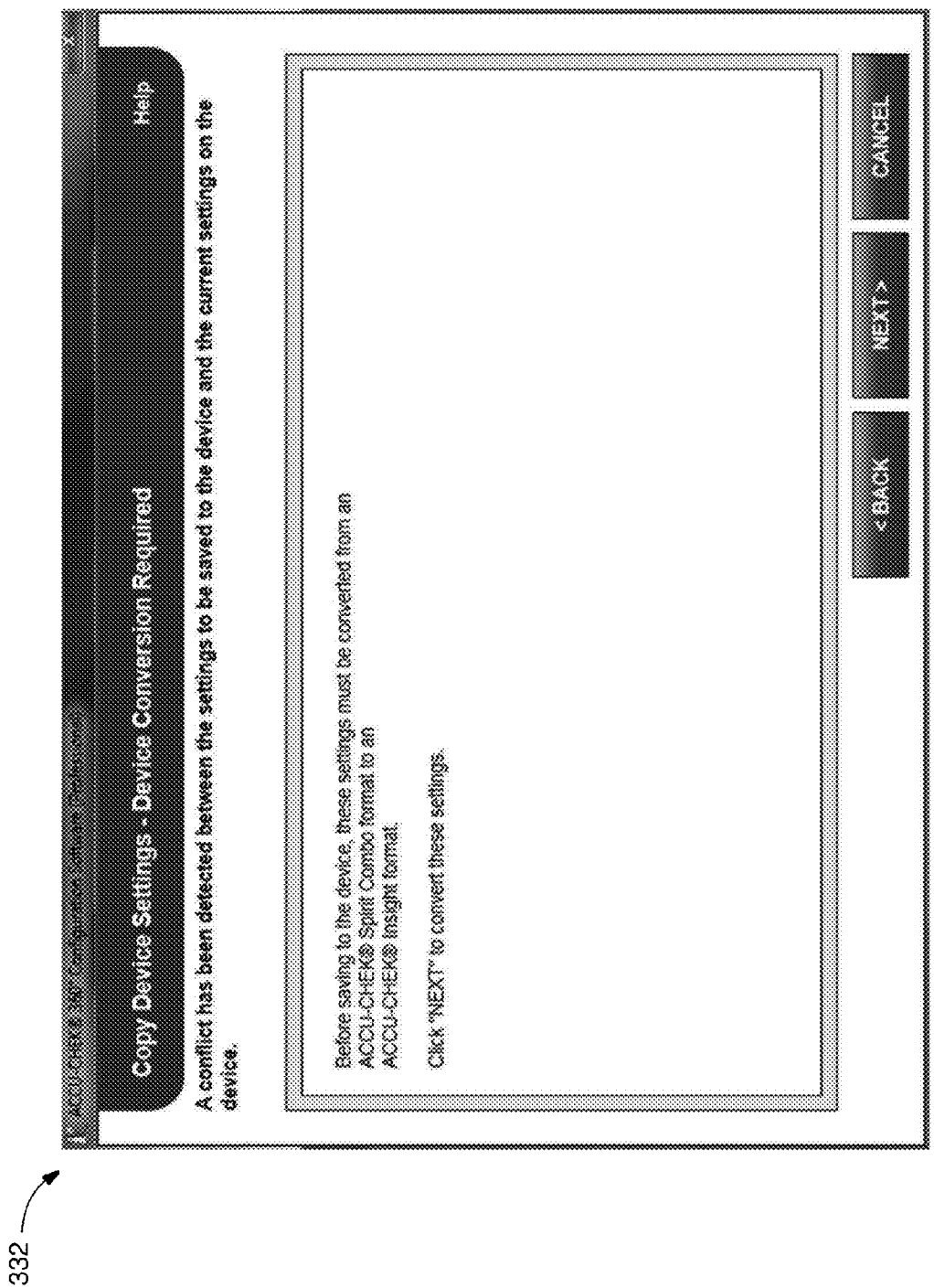
Figure 8C:
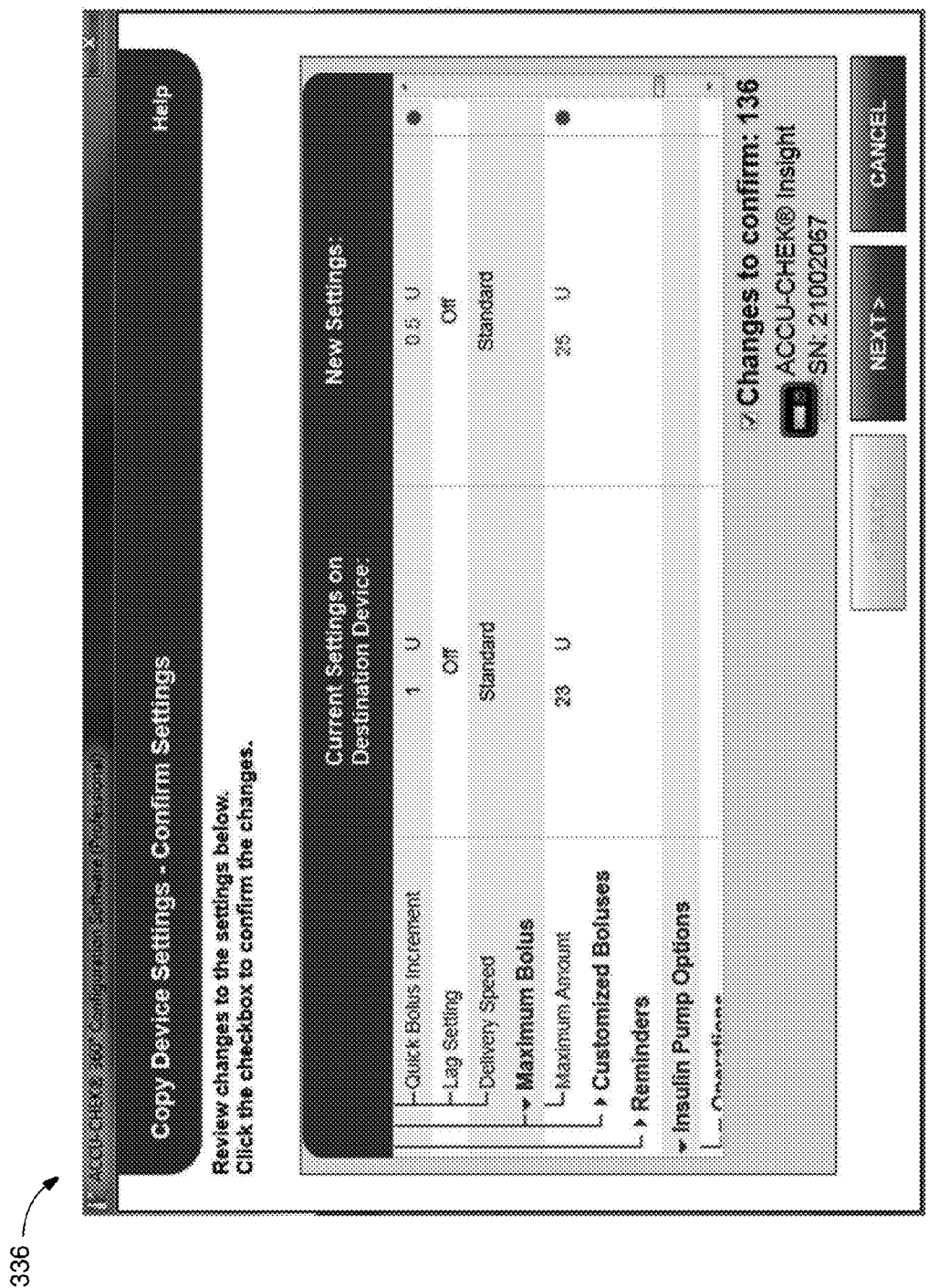
Figure 8D:
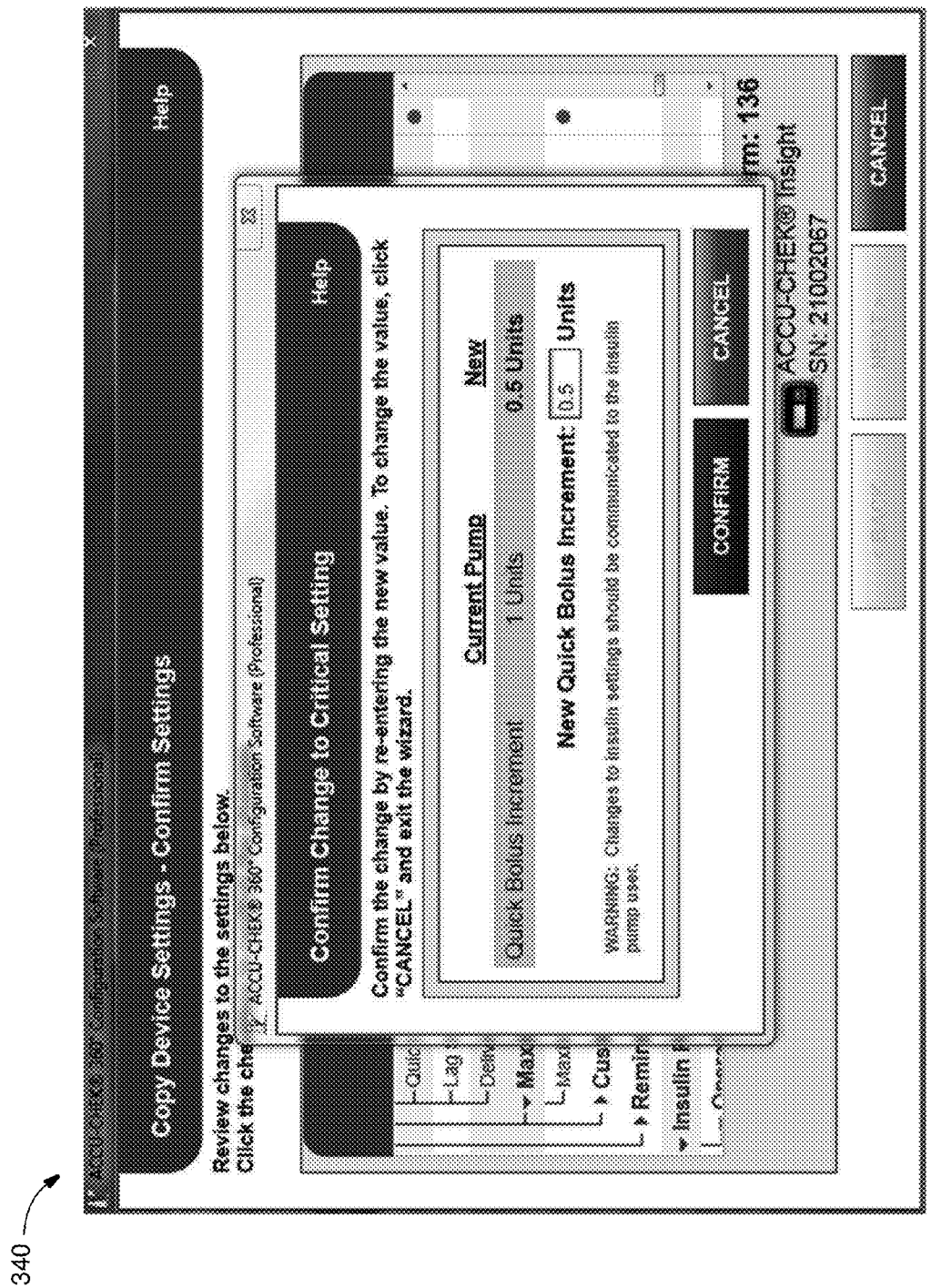
Figure 8E:
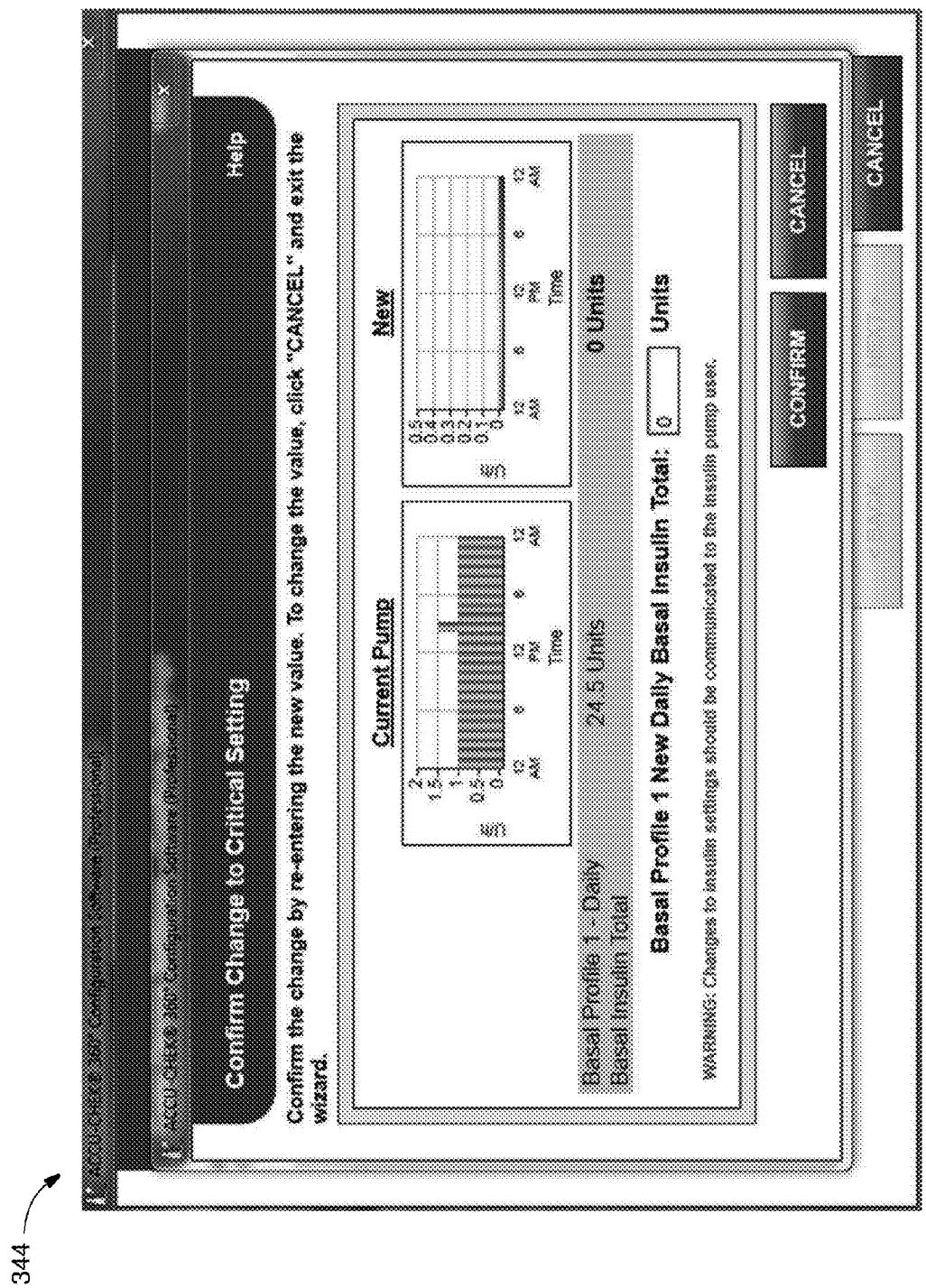
Figure 8F:
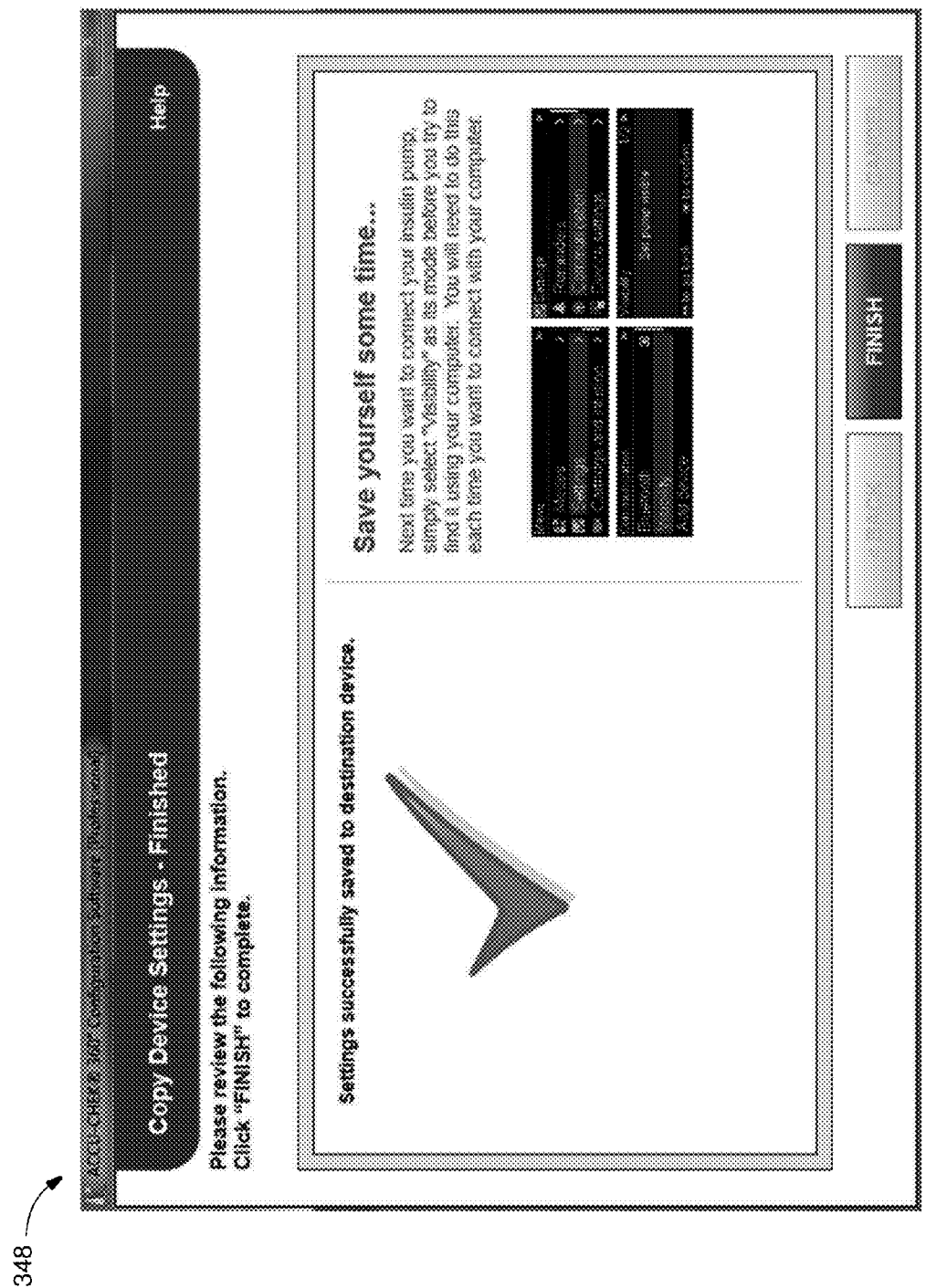

FIG. 5 depicts a startup screen 104 that instructs the operator to select one of a plurality of startup procedures, such as, "Read from Device", "Open from File", "Copy Device Settings", and "More Options". The copy settings module receives an operator selection, either via touch screen or any other suitable selection method. The copy settings module determines whether "Copy Device Settings" was selected based on the operator selection. The copy settings module generates and displays a copy device settings instructions screen 108. The instructions screen 108 displays to the operator "[t]o copy settings from one device to another, first select the device from which settings are to be copied (i.e., the "source" device). Then select the device to which the settings are to be copied (i.e., the "destination" device). Click "NEXT" to begin copying settings from the source device to the destination device."

In other words, the instructions screen 108 instructs the operator to select a source device, such as the source pump 24, and a destination device, such as the destination pump 25. The operator may then select "NEXT" or "CANCEL". The copy settings module determines whether the operator selected "NEXT" or "CANCEL". For example, when the operator selects "NEXT", the copy settings module receives a signal indicating that the operator selected "NEXT". The next signal may be a value that indicates the operator selected "NEXT", a high voltage signal, or any suitable indicator. Similarly, when the operator selects "CANCEL" the copy settings module receives a signal indicating the operator selected "CANCEL". The cancel signal may be any suitable signal including those listed above with respect to the next signal.

The copy settings module determines whether the operator selected "NEXT" or "CANCEL" based on the received signals. When the copy settings module determines the operator selected "CANCEL", the copy settings module generates and displays the startup screen 104. Alternatively, the copy settings module may generate and display a copy device settings cancellation warning dialog box 112. In one example, the warning dialog box 112 may inform the operator that "Copy Settings Canceled—No changes were made to the destination device." The operator may then select "OK" to confirm the cancellation.

When the copy settings module determines that the operator selected "NEXT", the copy settings module generates and displays a copy device settings preparation screen 204, as illustrated in FIG. 6. The preparation screen 204 presents the operator with an option to "[s]earch for a device" or "[h]elp me connect to a device." The preparation screen 204 instructs the operator to select one of the above options in order to select a source device, such as the source pump 24, by searching for a device connected to the computing device 12 or by receiving help finding standard and/or suggested devices.

The copy settings module determines whether the user selected to search for a device or receive help finding a device. It is understood that the copy settings module determines a selection made by the operator in a similar manner to that described above with respect to the "NEXT" and "CANCEL" selections. When the copy settings module determines the operator selected to search for a device, the copy settings module generates and displays a copy device settings looking for devices screen 208. The looking for devices screen 208 informs the operator that "[d]etected devices will be displayed as they are found. Select the desired source device below."

The looking for devices screen 208 displays a list of devices connected to the computing device 12. For example, the copy settings module detects pumps coupled to the computing device 12. The copy settings module generates a list of all devices connected to the computing device 12 and displays, in a copying device settings looking for devices screen 212, a list of pumps connected to the computing device 12. For example, the copy settings module detects the source pump 24 and displays an image of the source pump 24 along with any relevant information pertaining to the source pump 24. The relevant information may include the device name, type, and any other suitable information.

The operator selects a device from the list of devices displayed on the looking for devices screen 212. The copy settings module receives a device signal indicating a device the operator selected from the list of devices. The copy settings module determines which device the operator selected based on the device signal. The copy settings module may determine the operator selection by any means described above. In one example, the copy settings module determines the operator selected the source pump 24. When the copy settings module determines the operator has selected the source pump 24, the copy settings module generates and displays a copy device settings communication status screen 224. The status screen 224 informs the operator that "[c]ommunicating with selected device. Click "CANCEL" to stop."

Alternatively, when the copy settings module determines the operator selected to receive help finding a device, the copy settings module generates and displays a copy device settings select your device screen 216. The device screen 216 instructs the operator to "[s]elect the device you want to connect." The select your device screen 216 displays, to the operator, common devices that may include the device the operator desires to select as the source device.

The copy settings module receives a device signal indicating a device the operated selected. The copy settings module generates a copy device settings communication mode screen 220. For example, when the copy settings module determines the operator selected a source device, the copy settings module generates the communication mode screen 220 informing the operator that "[b]efore your device can communicate with your computer you must put it in communication mode." In other words, the copy settings module cannot determine the selected device type until the operator places the device in a communication mode.

Once the operator places the device in the communication mode, the copy settings module determines which device the operated selected based on communication with the device. The copy settings module displays the selected device type and relevant device information on the screen 220. The operator then reviews the relevant information about the source pump 24 and selects "NEXT". The operator may also select "BACK" to return to the previous screen 216 in order to select a different device or select "CANCEL".

When the copy settings module determines the operator selected "NEXT", the copy settings module generates the communication status screen 224. The communication status screen 224 informs the operator that the copy settings module is "[c]ommunicating with selected device. Click "CANCEL" to stop." In other words, the screen 224 illustrates to the operator a current communication status of the source pump 24 (i.e., whether or not the computing device 12 is communicating with the source pump 24.)

Once communication between the source pump 24 and the computing device 12 has been established, the copy settings module copies and/or reads the configuration file from the source pump 24. The copy settings module then generates and displays a copy device settings finished reading screen 228. The finished reading screen 228 informs the operator that "[s]ettings were successfully read from the source device. Put the device to which the settings are to be copied (i.e., the "destination" device) in communication mode. Click "NEXT" to continue."

The operator may then select "NEXT", "BACK", or "CANCEL" from the finished reading screen 228. As described above, the copy settings module determines whether a selection was made by the operator. When the copy settings module determines the operator selected "BACK", the copy settings module generates and displays the communication status screen 224. When the copy settings module determines the operator selected "CANCEL", the copy settings module generates and displays the cancellation warning dialog box 112, as described above. When the copy settings module determines the operator selected "NEXT", the copy settings module generates and displays a copy device settings preparation screen 304 as illustrated in FIG. 7.

As described above with reference to FIG. 6 with respect to the operator selecting a source device, such as the source pump 24, FIG. 7 illustrates the operator selecting a destination device, such as the destination pump 25. The preparation screen 304 instructs the operator to select a destination device, such as the destination pump 25, by searching for a devices connected to the computing device 12 or by receiving help finding standard and/or suggested devices as described above with reference to screen 204.

As described above, the copy settings module determines whether the user selected to search for a device or receive help finding a device. When the copy settings module determines the operator selected to search for a device, the copy settings module generates and displays a copy device settings looking for devices screen 308.

The looking for devices 308 informs the operator that "[d]etected devices will be displayed as they are found. Select the desired destination device below." The copy settings module generates a list of all devices connected to the computing device 12 and displays, in a copying device settings looking for devices screen 312, a list of pumps connected to the computing device 12. For example, the copy settings module detects the destination pump 25 and displays an image of the destination pump 25 along with any relevant information.

The operator selects a device from the list of devices displayed on the looking for devices screen 312. The copy settings module receives a device signal indicating the device the operator selected. The copy settings module determines which device the operator selected based on the device signal. In one example, the copy settings module determines the operator selected the destination pump 25. When the copy settings module determines the operator has selected the destination pump 25, the copy settings module generates and displays a copy device settings connecting screen 324.

Alternatively, when the copy settings module determines the operator selected to receive help finding a device, the copy settings module generates and displays a copy device settings select your device screen 316. The select your device screen 316 instructs the operator to "[s]elect the device you want to connect." The select your device screen 316 displays, to the operator, common devices that may include the device the operator desires to select as a destination device. The copy settings module generates and displays a copy device settings communication mode screen 220. For example, when the copy settings module determines the operator selected a destination device, the copy settings module generates the communication mode screen 320. The communication mode screen 320 informs the operator that "[b]efore your device can communicate with your computer you must put it in communication mode."

Alternatively, the communication mode screen 320 may instruct the operator to connect the destination pump 25 to a port on the computing device, such as a universal serial bus (USB) port. The operator then connects the destination pump 25 to the computing device and places the destination pump 25 in a communication mode. The copy settings module receives a device signal indicating the operator selected a device and determines, by communicating with the device, the device type. The copy settings module displays the device type and relevant information on the screen 320. The operator reviews the information and selects "NEXT". The operator may also select "BACK" to return to the previous screen 316 in order to select a different device or select "CANCEL".

When the copy settings module determines the operator selected "NEXT", the copy settings module generates the copy device settings connecting screen 324. The connecting screen 324 informs the operator that the copy settings module is "[c]onnecting to the device." In other words, the connecting screen 324 illustrates to the operator a current connection status of the destination pump 25 (i.e., whether or not the computing device 12 is communicating with the destination pump 25.)

Once communication between the destination pump 25 and the computing device 12 has been established, the copy settings module generates and displays a copy device settings communication status screen 328 as illustrated in FIG. 8. The status screen 328 informs the operator that the copy settings module is "[c]ommunicating with selected device. Click "CANCEL" to stop." In other words, the screen 328 illustrates to the operator a current status of the destination pump 25. The copy settings module applies the plurality of parameters copied from the source pump 24 to the destination pump 25. The status screen 328 may instruct the operator not to adjust and/or power off the destination pump 25 while the copy settings module is attempting to apply the copied configuration file from the source pump 24 to the destination pump 25.

The copy settings module determines whether a conflict exists between one or more parameters copied from the source pump 24 and one or more parameters on the destination pump 25. As it can be appreciated, because the many of the values corresponding to the plurality of parameters affect how a user of an insulin pump receives insulin and monitors blood glucose levels, it is critical that the operator understand the detected conflicts and either accepts the suggested resolution or manually adjust a value in order to resolve the conflict.

The operator must validate and/or resolve conflicts detected by the copy settings module. For example, the copy settings module maps each of the plurality of parameters copied from the source pump 24 to a corresponding parameter on the destination pump 25. In some examples, a parameter that was present on the source pump 24 does not have a one-to-one corresponding parameter on the destination pump 25, referred to hereinafter as a parameter mismatch. When the copy settings module determines a parameter mismatch occurred, the copy settings module generates and displays a copy device settings device conversion required screen 332. The conversion required screen 332 informs the operator "[a] conflict has been detected between the settings to be saved to the device and the current settings on the device."

The conversion required screen 332 also informs the operator that "[b]efore saving to the device, these settings must be converted . . . click "NEXT" to convert these settings." In some examples, the copy settings module may generate and display, in the conversion required screen 332, specific settings that must be converted. An example illustrated in the conversion required screen 332 includes converting from "ACCU-CHEK Spirit Combo format to an ACCU-CHEK Insight format." In this manner, the operator is informed of a parameter mismatch and what conversion must take place prior to saving the copied configuration file from the source pump 24 to the destination device 25.

The operator may then select "BACK", "NEXT", or "CANCEL". As described above, the copy settings module determines a selection made by the operator. When the copy settings module determines the operator selected "BACK", the copy settings module displays the communication status screen 328. When the copy settings module determines the operator selected "CANCEL", the copy settings module displays the startup screen 104 or alternatively the cancellation warning dialog box 112.

When the copy settings module determines the operator selected "NEXT", the copy settings module generates and displays a copy device settings confirm settings screen 336. The confirm settings screen 336 informs the operator to "[r]eview changes to the settings below. Click the checkbox to confirm the changes." As illustrated in the confirm settings screen 336, both parameter mismatches and parameters matches are displayed. For example, the confirm settings screen 336 informs the user, by way of non-limiting example only, that the Quick Bolus Increment parameter was set to 1 unit on the source pump 24. The confirm settings screen 336 informs the user of a suggested conversion for the Quick Bolus Increment parameter on the destination device 25 of 0.5 units. In other words, the confirm settings screen 336 displays a suggested conversion to correct a parameter mismatch detected by the copy settings module.

The confirm settings screen 336 also displays parameter matching information. For example, the confirm settings screen 336 informs the operator that a Delivery Speed parameter on the source pump 24 and the destination pump 25 will both be set to Standard. It is understood that while only limited examples are provided herein, the confirm settings screen 336 may display any suitable information that the operator may be instructed to confirm. The confirm settings screen 336 instructs the operator to confirm parameter settings displayed on the screen 336. In other words, the operator must click the checkbox displayed on the screen 336 before the operator has an option to select "NEXT". The operator may then select "NEXT" or "CANCEL".

As described above, when the copy settings module determines the operator selected "CANCEL" the copy settings module displays the startup screen 104 or alternatively the cancelation warning dialog box 112. When the copy settings module determines the operator selected "NEXT", the copy settings module generates and displays a confirm change to critical setting dialog box 340. It is understood that the confirm change to critical setting dialog box 340 may not be displayed in examples where no changes to critical settings are required. The dialog box 340 informs the operator to "[c]onfirm the change by re-entering the new value. To change the value, click "CANCEL" and exit the wizard." The dialog box 340 displays a value corresponding to a parameter copied from the source pump 24 and a difference between a source value and a destination value. In some examples, the operator may adjust the value corresponding to the difference between the source value and a destination value. In other examples, the operator re-enters the value in order to confirm that the operator understands the critical change being applied to the destination value.

By way of non-limiting example, the dialog box 340 displays a "Quick Bolus Increment" with a source pump 24 parameter value of 1 unit and a destination pump 25 parameter value of 0.5 units. The dialog box 340 instructs the user to review critical parameter changes and re-enter the suggested value in a "New Quick Bolus Increment" field. The operator may then re-enter the suggested value described above, or manually select a desired value and enter the desired value in the "New Quick Bolus Increment" field. The operator may then select "CONFIRM" or "CANCEL". As described above, when the copy settings module determines the operator selected "CANCEL", the copy settings module displays the startup screen 104 or alternatively, the cancellation warning dialog box 112.

When the copy settings module determines the operator selected "CONFIRM", the copy settings module generates and displays an additional confirm change to critical setting dialog box 344. The additional confirm change to critical setting dialog box 344 may display additional parameter conversions that the operator must confirm. For example, the dialog box 344 informs the operator that the source pump 24 has a Basal Profile 1. The Basal Profile 1 may track daily insulin units received by the user of the source pump 24. The dialog box 344 informs the operator that the Basal Profile 1 does not have a value associated with the Basal Profile 1 parameter on the destination pump 25. The operator may then manually enter a value in a "Basal Profile 1 New Daily Basal Insulin Total" field or accept the suggested value prepopulated in the "Basal Profile 1 New Daily Basal Insulin Total" field.

The operator then selects "CONFIRM" or "CANCEL". When the copy settings module determines the operator selected "CANCEL", the copy settings module proceeds as described above. When the copy settings module determines that the operator selected "CONFIRM", the copy settings module modifies a configuration file on the destination pump 25 by copying the values of each of the plurality of parameters from the configuration file from the source pump 24 to corresponding parameters within the configuration file on the destination pump 25.

The copy settings module then generates and displays a copy device settings finished screen 348. The finished screen 348 informs the operator to "[p]lease review the following information. Click "FINISH" to complete." Alternatively, in other examples, the finish screen 348 will simply instruct the operator to "Click "FINISH" to complete." The operator may then review the information and click "FINISH". When the copy settings module determines the operator has selected "FINISH", the copy settings module closes the finished reading screen 348.

Figure 9:
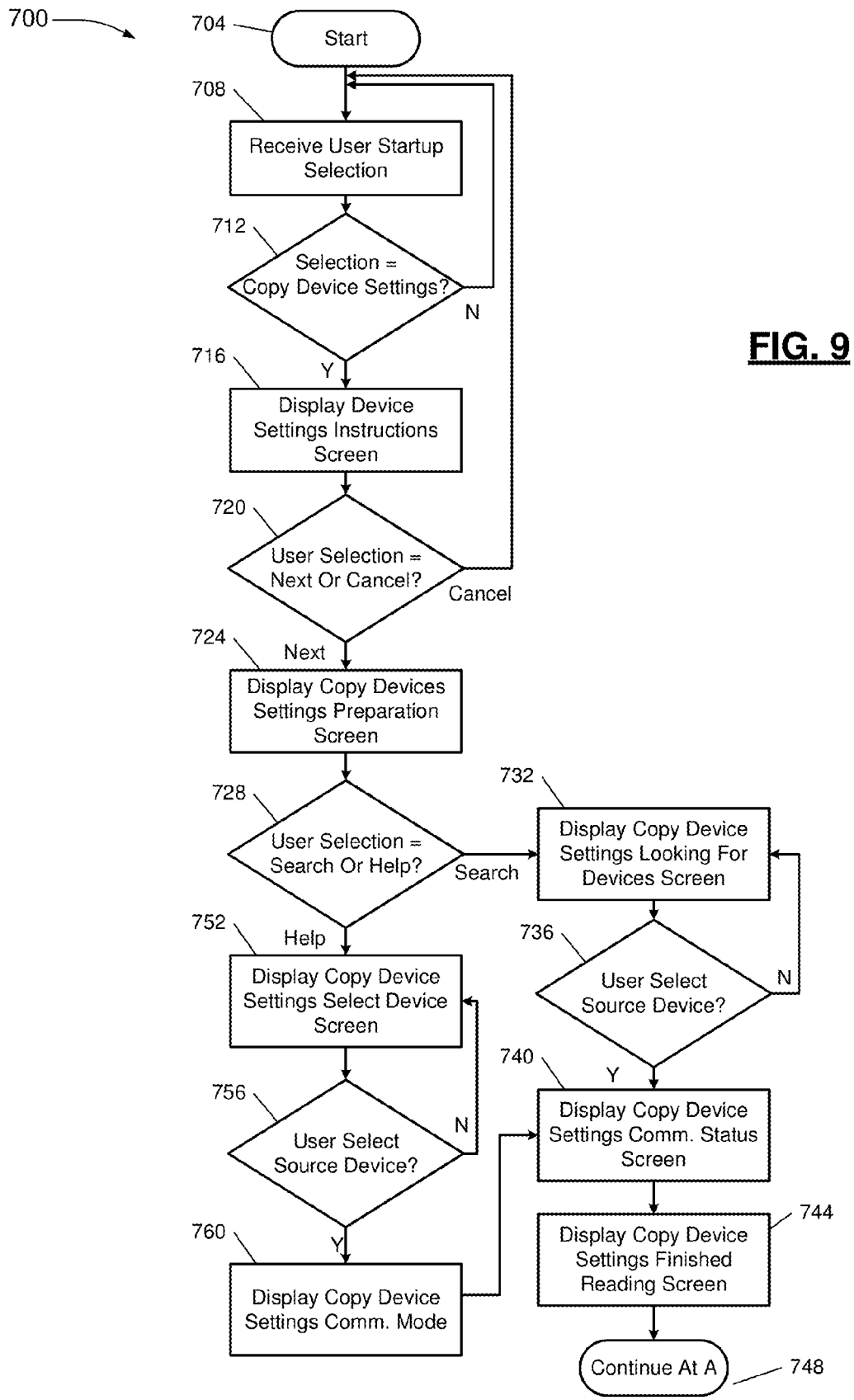
FIGS. 9-10 is a flow diagram of an example technique for interacting with an operator for copying parameters from a source device to a destination device according to the principles of the present disclosure.
Figure 10:
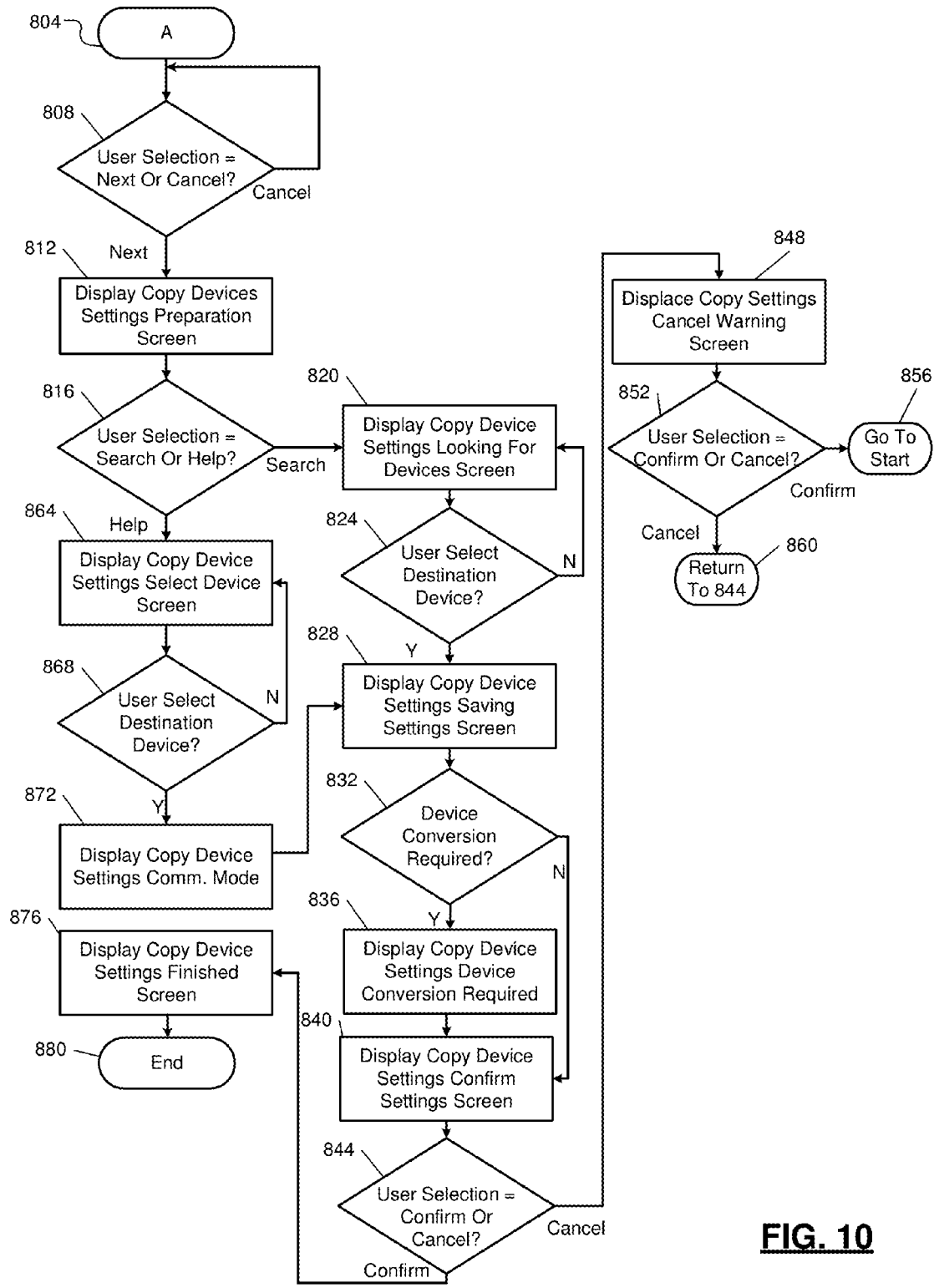

With reference to FIGS. 9 and 10, a flow diagram illustrating a method 700 executed by the copy settings module. The method 700 illustrates an example of copying parameters from a source pump to a destination pump begins at 704. At 708, the method 700 receives a startup selection. For example, the copy settings module receives the startup selection in response to the operator selecting one of the selections displayed on the startup screen 104.

At 712, the method 700 determines whether the startup select is the copy device settings selection. For example, the copy settings module receives a signal indicating the operator selection. The copy settings module determines whether the operator selection is the "Copy Device Settings" selection based on the signal. If false, the method 700 returns to 708. If true, the method 700 continues at 716. At 716, the method 700 displays a copy device settings instruction screen.

At 720, the method 700 determines whether an operator selected "NEXT" or "CANCEL" from the instructions screen. As described above, the copy settings module determines whether the operator selected "NEXT" based on a selection signal received from the instructions screen. If "CANCEL", the method 700 returns to 708. Alternatively, the method 700 may continue at 848. If "NEXT", the method 700 continues at 724.

At 724, the method 700 displays a copy devices settings preparation screen. At 728, the method 700 determines whether the operator selected "SEARCH" or "HELP" from the preparation screen. For example, the copy settings module determines whether the operator selected the "SEARCH" option from the preparation screen based on a signal received from the preparation screen. If "HELP", the method 700 continues at 752. If "SEARCH", the method 700 continues at 732.

At 732, the method 700 displays a copy devices settings looking for devices screen. At 736, the method 700 determines whether the operator selected a source device from a list of devices displayed on the looking for devices screen. As described above, the copy settings module determines whether the operator selected a device from the list of devices based on a device signal. If false, the method 700 returns to 732. If true, the method 700 continues at 740.

At 740, the method 700 displays a copy device settings communication status screen. For example, the copy settings module generates and displays a status indicating whether the copy settings module is copying the plurality of parameters from the source pump 24. At 744, the method 700 displays a copy device settings finished reading screen. The method 700 continues at 748.

At 752, the method 700 displays a copy device settings select device screen. At 756, the method 700 determines whether the operator selected a device from the select a device screen. For example, as described above, the copy settings module determines whether the operator selected a device based on a received device signal. If false, the method 700 continues at 752. If true, the method 700 continues at 760. At 760, the method 700 displays a copy device settings communication mode screen indicating to the operator that the selected source device must be placed in a communication mode. The method continues at 740.

At 748, the method 700 continues at 804. At 808, the method 700 determines whether the operator selected "NEXT" or "CANCEL" on the settings finished reading screen. If "CANCEL", the method 700 returns to 808. Alternatively, the method 700 continues at 848. If "NEXT", the method 700 continues at 812. At 812, the method 700 displays a copy devices setting preparation screen. At 816, the method 700 determines whether the operator selected "SEARCH" or "HELP" from the preparation screen. If "HELP", the method 700 continues at 864. If "SEARCH", the method 700 continues at 820.

At 820, the method 700 displays a copy devices settings looking for devices screen. At 824, the method 700 determines whether the operator selected a destination device from a list of devices displayed on the looking for devices screen. As described above, the copy settings module determines whether the operator selected a device based on a received device signal. If false, the method 700 returns to 820. If true, the method 700 continues at 828.

At 828, the method 700 displays a copy device setting saving settings screen. The saving settings screen indicates to the operator that the copy settings module is saving the copied parameters from the source pump 24 to the destination pump 25. At 832, the method determines whether a parameter mismatch occurred, as described above. If false, the method 700 continues at 840. If true, the method 700 continues at 836.

At 836, the method 700 displays a copy device settings device conversion required screen. For example, the copy settings module generates and displays a copy device settings device conversion required screen based on a determination that a parameter mismatch occurred. At 840, the method 700 displays a display copy device settings confirm settings screen. At 844, the method 700 determines whether the operator selected "CONFIRM" or "CANCEL" on the confirm settings screen. If "CANCEL", the method 700 continues at 848. If "CONFIRM" the method 700 continues at 876.

At 848, the method 700 displays a copy settings cancel warning screen. At 852, the method 700 determines whether the operator selected "CONFIRM" or "CANCEL" from the warning screen. If "CANCEL", the method returns to 844. If "CONFIRM", the method 700 returns to 704.

At 864, the method 700 displays a copy device settings select device screen. At 868, the method 700 determines whether the operator selected a destination device, such as the destination device 25, from the select a device screen. As described above, the copy settings module determines whether the operator selected a destination device based on a received device signal. If false, the method 700 continues at 864. If true, the method 700 continues at 872.

At 872, the method 700 displays a copy device settings communication mode screen indicating to the operator that the selected destination device must be placed in a communication mode. The copy settings module, in response to the destination device being places in a communications mode, copies values corresponding to a plurality of source parameters to corresponding destination parameters on the destination device. The method 700 continues at 828. At 876, the method 700 displays a copy device settings finished screen. At method 700 ends at 880.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

What is claimed is:

1. A system for configuring an insulin pump comprising:
 a source device having an associated source configuration file comprising a plurality of configurable source parameters;
 a destination device having an associated destination configuration file comprising a plurality of configurable destination parameters; and
 a computing device comprising a copy settings module configured to:
  be selectively in communication with the source device and the destination device,
  in response to receiving a first selection from an operator, retrieve the source configuration file, in response to receiving a second selection from the operator, retrieve the destination configuration file, identify parameter mismatches based on a comparison between each of the source parameters and each of the destination parameters, in response to identifying a parameter mismatch, display, on an operator viewable screen, a dialog box indicating at least one mismatched source parameter and a corresponding destination parameter, receive, via the dialog box, a source parameter conversion value, and copy values associated with each of the source parameters to corresponding destination parameters based on the parameter mismatches.

2. The system of claim 1 wherein the copy settings module identifies a parameter mismatch when, based on the comparison between each of the source parameters and each of the destination parameters, at least one source parameter does not match a corresponding destination parameter.

3. The system of claim 1 wherein the copy settings module copies the source parameter conversion value to the destination parameter corresponding to the at least one source parameter.

4. The system of claim 1 wherein the operator selects the source device from a plurality of devices connected to the computing device.

5. The system of claim 4 wherein the copy settings module instructs the operator to place the source device in a communication mode.

6. The system of claim 5 wherein the copy settings module retrieves the source configuration file in response to the source device being placed in the communication mode.

7. The system of claim 1 wherein the operator selects the destination device from a plurality of devices connected to the computing device.

8. The system of claim 7 wherein the copy settings module instructs the operator to place the destination device in a communication mode.

9. The system of claim 8 wherein the copy settings module retrieves the destination configuration file in response to the destination device being placed in the communication mode.

10. A method for configuring an insulin pump comprising:
receiving a source device selection from an operator;
identifying a source device based on the source device selection, the source device having an associated source configuration file comprising a plurality of configurable source parameters;
receiving a destination device selection from the operator;
identifying a destination device based on the destination device selection, the destination device having an associated destination configuration file comprising a plurality of configurable destination parameters;
selectively communicating with the source device and the destination device;
retrieving, in response to receiving the source device selection, the source configuration file;
retrieving, in response to receiving the destination device selection, the destination configuration file;
comparing each of the source parameters to each of the destination parameters;
identifying parameter mismatches based on the comparison between each of the source parameters and each of the destination parameters;
in response to identifying a parameter mismatch, display, on an operator viewable screen, a dialog box indicating at least one mismatched source parameter and corresponding destination parameter;
receiving, via the dialog box, a source parameter conversion value; and
copying values associated with each of the source parameters to corresponding destination parameters based on the parameter mismatches.

11. The method of claim 10 further comprising identifying a parameter mismatch when, based on the comparison between each of the source parameters and each of the destination parameters, at least one source parameter does not match a corresponding destination parameter.

12. The method of claim 10 further comprising copying the source parameter conversion value to the destination parameter corresponding to the at least one source parameter.

13. The method of claim 10 further comprising instructing the operator to place the source device in a communication mode.

14. The method of claim 13 further comprising retrieving the source configuration file in response to the source device being placed in the communication mode.

15. The method of claim 10 further comprising instructing the operator to place the destination device in a communication mode.

16. The method of claim 15 further comprising retrieving the destination configuration file in response to the destination device being placed in the communication mode.

17. A system for configuring an insulin pump comprising:
a source infusion pump having an associated source configuration file comprising a plurality of configurable source parameters;
a destination infusion pump having an associated destination configuration file comprising a plurality of configurable destination parameters; and
a computing device comprising a copy settings module configured to:
be selectively in communication with the source infusion pump and the destination infusion pump,
in response to receiving a first selection from an operator, retrieve the source configuration file,
in response to receiving a second selection from the operator, retrieve the destination configuration file,
identify parameter mismatches based on a comparison between each of the source parameters and each of the destination parameters,
in response to identifying a parameter mismatch, display, on an operator viewable screen, a dialog box indicating at least one mismatched source parameter and a corresponding destination parameter,
receive, via the dialog box, a source parameter conversion value, and
copy values associated with each of the source parameters to corresponding destination parameters based on the parameter mismatches.

18. The system of claim 17 wherein the copy settings module copies the source parameter conversion value to the destination parameter corresponding to the at least one source parameter.

19. The system of claim 17, wherein the copy settings module is configured to:
instruct the operator to place the source infusion pump in a communication mode, and
retrieve the source configuration file in response to the source infusion pump being placed in the communication mode.

20. The system of claim 17, wherein the copy settings module is configured to:
  instruct the operator to place the destination infusion pump in a communication mode, and
  retrieve the destination configuration file in response to the destination infusion pump being placed in the communication mode.

* * * * *